US007902199B2

(12) United States Patent
Rosenblum et al.

(10) Patent No.: US 7,902,199 B2
(45) Date of Patent: Mar. 8, 2011

(54) HETEROCYCLIC SUBSTITUTED PIPERAZINE COMPOUNDS WITH CXCR3 ANTAGONIST ACTIVITY

(75) Inventors: Stuart B. Rosenblum, West Orange, NJ (US); Joseph A. Kozlowski, Princeton, NJ (US); Neng-Yang Shih, Warren, NJ (US); Brian F. McGuinness, Plainsboro, NJ (US); Douglas W. Hobbs, Chesterfield, MO (US)

(73) Assignees: Schering Corporation, Kenilworth, NJ (US); Pharmacopeia, Inc., Princeton, NJ (US)

( * ) Notice: Subject to any disclaimer, the term of this patent is extended or adjusted under 35 U.S.C. 154(b) by 0 days.

(21) Appl. No.: 11/776,901

(22) Filed: Jul. 12, 2007

(65) Prior Publication Data

US 2008/0058343 A1 Mar. 6, 2008

Related U.S. Application Data

(60) Provisional application No. 60/831,053, filed on Jul. 14, 2006.

(51) Int. Cl.
*A61K 31/496* (2006.01)
*C07D 401/12* (2006.01)
*C07D 401/14* (2006.01)

(52) U.S. Cl. .................................. 514/253.13; 544/364
(58) Field of Classification Search ........................ None
See application file for complete search history.

(56) References Cited

U.S. PATENT DOCUMENTS

| 6,124,319 A | 9/2000 | MacCoss et al. |
| 6,469,002 B1 | 10/2002 | Ohshima et al. |
| 6,794,379 B2 | 9/2004 | Medina et al. |
| 7,417,045 B2 | 8/2008 | Anilkumar et al. |
| 7,566,718 B2 | 7/2009 | Wong et al. |
| 2002/0018776 A1 | 2/2002 | Hancock |
| 2003/0055054 A1 | 3/2003 | Medina et al. |
| 2006/0036093 A1 | 2/2006 | Lin et al. |
| 2006/0276448 A1 | 12/2006 | Zeng et al. |
| 2006/0276457 A1 | 12/2006 | Yu et al. |
| 2006/0276479 A1 | 12/2006 | Kim et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2008/0039474 A1* | 2/2008 | Rosenblum et al. ...... 514/253.01 |
| 2008/0292589 A1 | 11/2008 | Anilkumar et al. |

FOREIGN PATENT DOCUMENTS

| WO | WO93/10091 | 5/1993 |
| WO | WO99/20606 | 4/1999 |
| WO | WO02/085861 | 10/2002 |
| WO | WO03/070242 | 8/2003 |
| WO | WO03/082335 | 10/2003 |
| WO | WO03/098185 | 11/2003 |
| WO | WO03/101970 | 12/2003 |
| WO | WO2004/074273 | 9/2004 |
| WO | WO2004/074278 | 9/2004 |
| WO | WO2004/074287 | 9/2004 |
| WO | WO2004/113323 | 12/2004 |
| WO | WO2005/077369 | 8/2005 |
| WO | WO2007/109238 | 9/2007 |
| WO | WO2008/079279 | 7/2008 |

OTHER PUBLICATIONS

International Search Report for PCT/US2007/015924 dated Nov. 16, 2007.
Angiolilo, Anne L., et al.; "Human Interferon-inducible Protein 10 is a Potent Inhibitor of Angiogenesis In Vivo"; The Journal of Experimental Medicine; 182:155-162 (1995).
Baggiolini, Marco, et al.; "Interleukin-8 and Related Chemotactic Cytokines—CXC and CC Chemokines"; Advances in Immunol.; 55:97-179 (1994).
Baggiolini, Marco, et al.; "CC chemokines in allergic inflammation"; Immunology Today; 15(3):127-133 (1994).
Clark-Lewis, Ian, et al.; "Structure-Activity Relationships of Interleukin-8 Determined Using Chemically Synthesized Analogs"; The Journal of Biological Chemistry; 266(34):23128-23134 (1991).

(Continued)

*Primary Examiner* — Emily Bernhardt
(74) *Attorney, Agent, or Firm* — Erik A. Meade; Krishna G. Banerjee

(57) ABSTRACT

The present application discloses a compound, or enantiomers, stereoisomers, rotamers, tautomers, racemates or prodrug of said compound, or pharmaceutically acceptable salts, solvates or esters of said compound, or of said prodrug, said compound having the general structure shown in Formula 1:

Formula 1

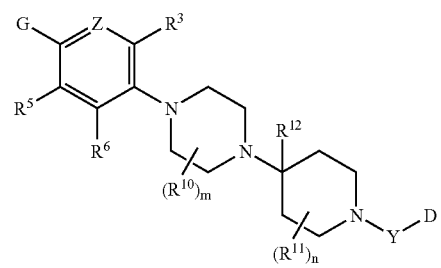

or a pharmaceutically acceptable salt, solvate or ester thereof. Also disclosed is a method of treating chemokine mediated diseases, such as, palliative therapy, curative therapy, prophylactic therapy of certain diseases and conditions such as inflammatory diseases (non-limiting example(s) include, psoriasis), autoimmune diseases (non-limiting example(s) include, rheumatoid arthritis, multiple sclerosis), graft rejection (non-limiting example(s) include, allograft rejection, zenograft rejection), infectious diseases (e.g., tuberculoid leprosy), fixed drug eruptions, cutaneous delayed-type hypersensitivity responses, ophthalmic inflammation, type I diabetes, viral meningitis and tumors using a compound of Formula 1.

40 Claims, No Drawings

OTHER PUBLICATIONS

Clark-Lewis, Ian, et al.; "Platelet factor 4 binds to interleukin 8 receptors and activates neutrophils when its N terminus is modified with Glu-Leu-Arg"; Proc. Natl. Acad. Sci. USA; 90:3574-3577 (1993).

Cole, Katherine E., et al.; "Interferon-inducible T Cell Alpha Chemoattractant (I-TAC): A Novel Non-ELR CXC Chemokine with Potent Activity on Activated T Cells through Selective High Affinity Binding to CXCR3"; J. Exp. Med.; 187(12):2009-2021 (1998).

Farber, Joshua M.; "A macrophage mRNA selectively induced by γ-interferon encodes a member of the platelet factor 4 family of cytokines"; Proc. Natl. Acad. Sci. USA; 87:5238-5242 (1990).

Farber, Joshua M.; "HuMIG: A New Human Member of the Chemokine Family of Cytokines"; Biochemical and Biophysical Research Communications; 192(1):223-230 (1993).

Galy, Anne H. M., et al.; "IL-1, IL-4, and IFN-γ Differentially Regulate Cytokine Production and Cell Surface Molecule Expression in Cultured Human Thymic Epithelial Cells"; The Journal of Immunology; 147(11):3823-3830 (1991).

Hebert, Caroline A., et al.; "Scanning Mutagenesis of Interleukin-8 Identifies a Cluster of Residues Required for Receptor Binding"; The Journal of Biological Chemistry; 266(28):18989-18994 (1991).

Liao, Fang, et al.; "Human Mig Chemokine: Biochemical and Functional Characterization"; J. Exp. Med.; 182:1301-1314 (1995).

Loetscher, Marcel, et al.; "Chemokine Receptor Specific for IP10 and Mig: Structure, Function, and Expression in Activated T-Lymphocytes"; J. Exp. Med.; 184:963-969 (1996).

Loetscher, Pius, et al.; "Monocyte chemotactic proteins MCP-1, MCP-2, and MCP-3 are major attractants for human CD4+ and CD8+ T lymphocytes"; FASEB J.; 8:1055-1060 (1994).

Luster, Andrew D., et al.; "IP-10, a-C-X-C- Chemokine, Elicits a Potent Thymus-dependent Antitumor Response In Vivo"; J. Exp. Med.; 178:1057-1065 (1993).

Luster, Andrew D., et al.; "The IP-10 Chemokine Binds to a Specific Cell Surface Heparan Sulfate Site Shared with Platelet Factor 4 and Inhibits Endothelial Cell Proliferation"; J. Exp. Med.; 182:219-231 (1995).

Luster, Andrew D., et al.; "γ-Interferon transcriptionally regulates an early-response gene containing homology to platelet proteins"; Nature; 315:672-676 (1985).

Qin, Shixin, et al.; "The Chemokine Receptors CXCR3 and CCR5 Mark Subsets of T Cells Associated with Certain Inflammatory Reactions"; J. Clin. Invest.; 101(4):746-754 (1998).

Schall, Thomas J., et al.; "Hemokines, leukocyte trafficking, and inflammation"; Current Opinion in Immunology; 6:865-873 (1994).

Seitz, Michael, et al.;. "Enhanced Production of Neutrophil-activating Peptide-1/Interleukin-8 in Rheumatoid Arthritis"; Journal Clin. Invest.; 87:463-469 (1991).

Springer, Timothy A.; "Traffic Signals on Endothelium for Lymphocyte Recirculation and Leukocyte Emigration"; Annu. Rev. Physiol.; 57:827-872 (1995).

Taub, Dennis D., et al.; "Recombinant Human Interferon-inducible Protein 10 is a Chemoattractant for Human Monocytes and T Lymphocytes and Promotes T Cell Adhesion to Endothelial Cells"; The Journal of Experimental Medicine; 177:1809-1814 (1993).

Taub, Dennis D., et al.; "α and β Chemokines Induce NK Cell Migration and Enhance NK-Mediated Cytolysis"; The Journal of Immunol.; 155:3877-3888 (1995).

Uguccioni, Mariagrazia, et al.; "Actions of the chemotactic cytokines MCP-1, MCP-2, MCP-3, Rantes, MIP-1α and MIP-1γ on human monocytes"; Eur. J. Immunol.; 25:64-68 (1995).

Wenshen Yu et al., U.S. Appl. No. 11/353,806; Notice of Allowance—mailed Aug. 24, 2009.

Preliminary Amendment for U.S. Appl. No. 12/519,970, submitted Jun. 18, 2009.

The Notice of Allowance and Fee(s) Due issued for U.S. Appl. No. 11/353,697 which published as U.S. Publication No. US2007/0021611.

* cited by examiner

HETEROCYCLIC SUBSTITUTED PIPERAZINE COMPOUNDS WITH CXCR3 ANTAGONIST ACTIVITY

This application claims the benefit of U.S. Provisional Application Ser. No. 60/831,053 filed Jul. 14, 2006, which is incorporated herein by reference in its entirety.

FIELD OF THE INVENTION

The present invention relates to novel heterocyclic substituted piperazines with CXCR3 antagonist activity, pharmaceutical compositions containing one or more such antagonists, one or more such antagonists in combination with other compounds with chemokine activity, one or more such antagonists in combination with known immunosuppressive agents, non-limiting example(s) include Methotrexate, interferon, cyclosporin, FK-506 and FTY720, methods of preparing such antagonists and methods of using such antagonists to modulate CXCR3 activity. This invention also discloses methods of using such CXCR3 antagonists for the treatment (non-limiting examples include palliative, curative and prophylactic therapies) of diseases and conditions where CXCR3 has been implicated. Diseases and conditions where CXCR3 has been implicated include but are not limited to inflammatory conditions (psoriasis and inflammatory bowel disease), autoimmune disease (multiple sclerosis, rheumatoid arthritis), fixed drug eruptions, cutaneous delayed-type hypersensitivity responses, type I diabetes, viral meningitis and tuberculoid leprosy. CXCR3 antagonist activity has also been indicated as a therapy for tumor growth suppression as well as graft rejection (allograft and zenograft rejections for example).

BACKGROUND OF THE INVENTION

Chemokines constitute a family of cytokines that are produced in inflammation and regulate leukocyte recruitment (Baggiolini, M. et al, *Adv. Immunol.*, 55; 97-179 (1994); Springer, T. A., *Annual Rev. Physio.*, 57: 827-872 (1995); and Schall, T. J. and K. B. Bacon, *Curr. Opin. Immunol*, 6: 865-873 (1994)). Chemokines are capable of selectively inducing chemotaxis of the formed elements of the blood (other than red blood cells), including leukocytes such as neutrophils, monocytes, macrophages, eosinophius, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

Chemokines are related in primary structure and share four conserved cysteines, which form disulfide bonds. Based upon this conserved cysteine motif, the family can be divided into distinct branches, including the C—X—C chemokines (α-chemokines) in which the first two conserved cysteines are separated by an intervening residue (e.g., IL-8, IP-10, Mig, I-TAC, PF4, ENA-78, GCP-2, GROα, GROβ, GROδ, NAP-2, NAP-4), and the C—C chemokines (β-chemokines), in which the first two conserved cysteines are adjacent residues (e.g., MIP-1α, MIP-1β, RANTES, MICP-1, MCP-2, MCP-3, I-309) (Baggiolini, M. and Dahinden, C. A., *Immunology Today*, 15: 127-133 (1994)). Most CXC-chemokines attract neutrophil leukocytes. For example, the CXC-chemokines interleukin-8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes.

CC-chemokines are generally less selective and can attract a variety of leukocyte cell types, including monocytes, eosinophils, basophils, T lymphocytes and natural killer cells. CC-chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils, A chemokine receptor that binds the CXC-chemokines IP-10 and Mig has been cloned, characterized (Loetscher, M. et al., *J. Exp. Med.*, 184: 963-969 (1996)) and designated CXCR3. CXCR3 is a G-protein coupled receptor with seven transmembrane-spanning domains and has been shown to be restrictively expressed in activated T cells, preferentially human Th1 cells. On binding of the appropriate ligand, chemokine receptors transduce an intracellular signal through the associated G-protein resulting in a rapid increase in intracellular calcium concentration.

The CXCR3 receptor mediates $Ca^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-1α, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009-2021 (1998)).

The restricted expression of human CXCR3 in activated T lymphocytes and the ligand selectivity of CXCR3 are noteworthy. The human receptor is highly expressed in IL-2 activated T lymphocytes, but was not detected in resting T lymphocytes, monocytes or granulocytes (Gin, S. et al., *J. Clin. Invest.*, 101: 746-754 (1998)). Additional studies of receptor distribution indicate that it is mostly CD3$^+$ cells that express CXCR3, including cells which are CD95$^+$, CD45RO$^+$, and CD45RA$^{low}$, a phenotype consistent with previous activation, although a proportion of CD20$^+$ (B) cells and CD56$^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J. Exp. Med.*, 177: 18090-1814 (1993); Taub, D. D. et al., *J.*

*Immunol.*, 155: 3877-3888 (1995); Cole, K. E. et al., *J. Exp. Med.*, 187: 2009-2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128-23134 (1991); Hebert, C. A. et al., *J. Biol. Chem.*, 266: 18989-18994 (1991); and Clark-Lewis, 1. et al., *Proc. Natl. Acad. Sci. USA*, 90: 3574-3577 (1993)). In addition, both recombinant human Mig and recombinant human IP-10 have been reported to induce calcium flux in tumor infiltrating lymphocytes (TIL) (Liao, F. et al., *J Exp. Med,* 182 1301-1314 (1995)). While IP-10 has been reported to induce chemotaxis of monocytes in vitro (Taub, D. D. et al. *J. Exp. Med.*, 177: 1809-1814 (1993), the receptor responsible has not been identified), human Mig and I-TAC appear highly selective, and do not show such an effect (Liao, F. et al., *J. Exp. Med.*, 182: 1301-1314 (1995); Cole, K. E. et al., *J. Exp. Med.*, 187: 2009-2021 (1998)). IP-10 expression is induced in a variety of tissues in inflammatory conditions such as psoriasis, fixed drug eruptions, cutaneous delayed-type hypersensitivity responses and tuberculoid leprosy as well as tumors and in animal model studies, for example, experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.,* 178: 1057-1065 (1993); Luster, A. D. et al., *J Exp. Med.* 182: 219-231 (1995); Angiolillo, A. L. et al., *J. Exp. Med.,* 182: 155-162 (1995); Taub, D. D. et al., *J. Immunol.,* 155: 3877-3888 (1995)). The expression patterns of IP-10, Mig and I-TAC are also distinct from that of other CXC chemokines in that expression of each is induced by interferon-gamma (IFNδ), while the expression of IL-8 is down-regulated by IFNδ (Luster, A. D. et al., *Nature,* 315: 672-676 (1985); Farber, J. M., *Proc. Natl. Acad. Sci. USA,* 87: 5238-5242 (1990); Farber, J. M., *Biochem. Biophys. Res. Commun.,* 192 (1): 223-230 (1993), Liao, F. et al., *J. Exp. Med.*, 182: 1301-1314 (1995); Seitz, M. et al., *J. Clin. Invest.,* 87: 463-469 (1991); Galy, A. H. M. and H. Spits, *J. Immunol.,* 147: 3823-3830 (1991); Cole, K. E. et al., *J. Exp. Med.,* 187: 2009-2021 (1998)).

Chemokines are recognized as the long-sought mediators for the recruitment of lymphocytes. Several CC-chemokines were found to elicit lymphocyte chemotaxis (Loetscher, P. et al., *FASEB J.,* 8: 1055-1060 (1994)), however, they are also active on granulocytes and monocytes (Uguccioni, M. et al., *Eur. J. Immunol.,* 25: 64-68 (1995); Baggiolini, M. and C. A. Dahinden, *Immunol. Today,* 15: 127-133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes. Accordingly, activated and effector T cells have been implicated in a number of disease states such as graft-rejection, inflammation, rheumatoid arthritis, multiple sclerosis, inflammatory bowel disease and psoriasis. Thus, CXCR3 represents a promising target for the development of novel therapeutics.

Reference is made to PCT Publication No. WO 93110091 (Applicant: Glaxo Group Limited, Published May 27, 1993) which discloses piperidine acetic acid derivatives as inhibitors of fibrinogen-dependent blood platelet aggregation having the formula:

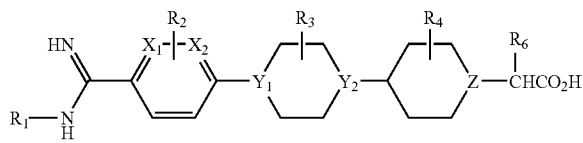

An illustrative compound of that series is:

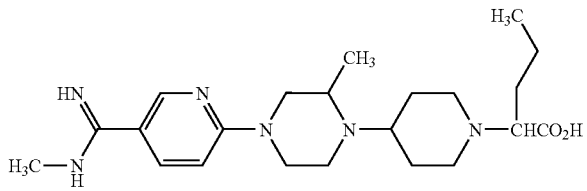

Reference is also made to PCT Publication No. WO 99/20606 (Applicant: J. Uriach & CIA. S. A., Published Apr. 29, 1999) which discloses piperazines as platelet aggregation inhibitors having the formula:

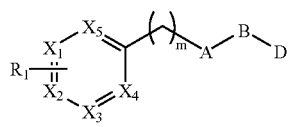

Reference is also made to US Patent Application No. US 2002/0018776 A1 (Applicant. Hancock, et al. Published Feb. 14, 2002) which discloses methods of treating graft rejection.

Reference is also made to PCT Publication No. WO 031098185 A2 (Applicant: Renovar, Inc., Published Nov. 27, 2003) which discloses methods of diagnosing and predicting organ transplant rejection by detection of chemokines, for example, CXCR3 and CCL chemokines in urine.

Reference is also made to PCT Publication No. WO 03/082335 A1 (Applicant: Sumitomo Pharmaceuticals Co. Ltd., Published Oct. 9, 2003) which discloses methods of screening a CXCR3 ligand and methods of diagnosing type 2 diabetes by detecting the expression dose of a CXCR3 ligand in a biological sample.

Reference is also made to PCT Publication No. WO 02/085861 (Applicant: Millennium Pharmaceuticals, Inc. Published Oct. 31, 2002) which discloses imidazolidine compounds and their use as CXCR3 antagonists having the formula:

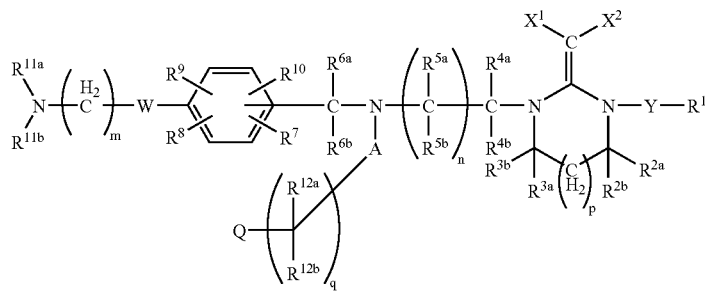

An illustrative compound of that series is:

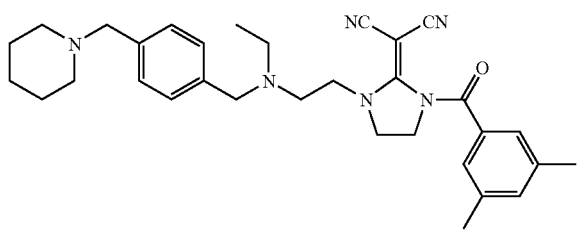

Reference is also made to PCT Publication No. WO 03/101970 (Applicant: SmithKline Beecham Corporation, Published Dec. 11, 2003) which discloses imidazolium compounds and their use as CXCR3 antagonists having the formula:

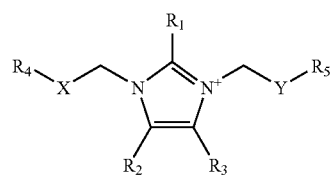

An illustrative example of that series is:

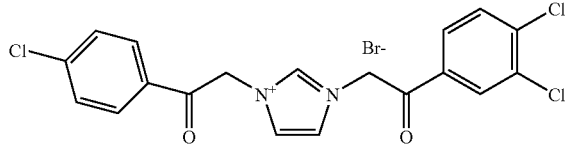

Reference is also made to US Patent Application No. US 2003/0055054 A1 (Applicant: Medina et al., Published Mar. 20, 2003) and related patent U.S. Pat. No. 6,794,379 B2 ((Applicant: Medina et al, Published Sep. 21, 2004) which discloses compounds with CXCR3 activity having the formula:

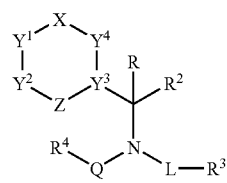

An illustrative compound of that series is:

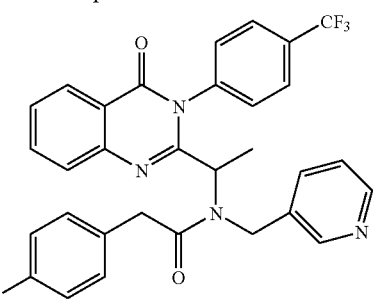

Reference is also made to U.S. Pat. No. 6,124,319 (Applicant: MacCoss et al., issued Sep. 6, 2000) which discloses compounds useful as chemokine receptor modulators having the formula:

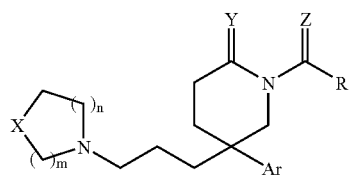

Reference is also made to PCT Publication WO 03/070242 A1 (Applicant: CELLTECH R&D limited, Published Aug. 28, 2003) which discloses compounds useful as "chemokine receptor inhibitors for the treatment of inflammatory diseases" having the formula:

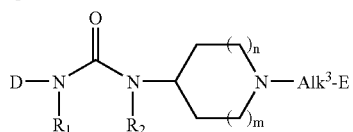

Reference is also made to PCT Publication WO 041074287 A1, WO 04/074273 A1, WO 04/74278 (Applicant: AstraZeneca R&D Published Feb. 19, 2004) which discloses pyridine derivatives, processes for their preparation and use in the modulation of autoimmune disease, having the formula.

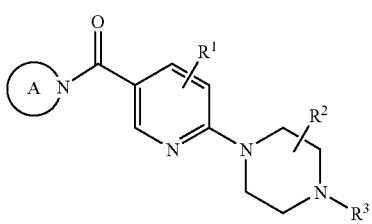

where R3 is phenyl, or a 5- or 6-membered aromatic ring with 1 or more nitrogen atoms.

Reference is also made to U.S. Patent Application Publication US2006/0036093 A1, published Feb. 16, 2006, which refers to certain pyrimidone compounds binding to CXCR3 receptors.

There is a need for compounds that are capable of modulating CXCR3 activity. For example, there is a need for new treatments and therapies for diseases and conditions associated with CXCR3 such as inflammatory conditions (psoriasis and inflammatory bowel disease), autoimmune disease (multiple sclerosis, rheumatoid arthritis) and graft rejection (allograft and zenograft rejections for example) as well as infectious diseases, cancers and tumors, fixed drug eruptions, cutaneous delayed-type hypersensitivity responses, type I diabetes, viral meningitis and tuberculoid leprosy.

There is a need for methods of treatment or prevention or amelioration of one or more symptoms of diseases and conditions associated with CXCR3. There is a need for methods for modulating CXCR3 activity using the compounds provided herein.

SUMMARY OF THE INVENTION

In its many embodiments, the invention provides novel compounds of Formula 1:

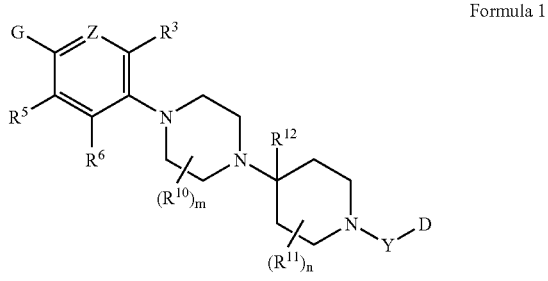

Formula 1 or a pharmaceutically acceptable salt, solvate or ester thereof wherein:

G is —C≡N or

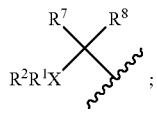

X is N, O, alkyl, cycloalkyl, heteroaryl, heterocyclyl or heteroalkyl;

Z is N, or NO;

$R^1$ and $R^2$ are independently absent or present, and if present each is independently selected from the group consisting of H, alkyl, alkoxy, alkenyl, cycloalkyl, cycloalkenyl, alkylaryl, arylalkyl, aryl, amino, -alkylamino, amidinyl, carboxamido, cyano, hydroxyl, urea, —N≡CH, =NCN, —$(CH_2)_q$OH, —$(CH_2)_q$O$R^{31}$, —$(CH_2)_q$N$H_2$, —$(CH_2)_q$NH$R^{31}$, —$(CH_2)_q$N($R^{31})_2$, —$(CH_2)_q$C(=O)NH$R^{31}$, —$(CH_2)_q$SO$_2R^{31}$, —$(CH_2)_q$NHSO$_2R^{31}$, —$(CH_2)_q$SO$_2$NH$R^{31}$, —C(=S)N(H)alkyl, —N(H)—S(O)$_2$-alkyl, —N(H)C(=O)N(H)-alkyl, —S(O)$_2$alkyl, —S(O)$_2$N(H)alkyl, —S(O)$_2$N(alkyl)$_2$, —S(O)$_2$aryl, —C(=S)N(H)cycloalkyl, —C(=O)N(H)NH$_2$, —C(=O)alkyl, —C(=O)aryl, —C(=O)heteroalkyl, heteroaryl, heterocyclyl, and heterocyclenyl; or alternatively when X is N, the N taken together with the $R^1$ and $R^2$ forms a cycloalkyl, heterocyclyl, heteroaryl or —N=C(NH$_2$)$_2$, $R^3$, $R^5$ and $R^6$ moieties can be the same or different, each being independently selected from the group consisting of H, alkyl, alkylaryl, aralkyl, —C(=O)alkyl, —CN, CF$_3$, OCF$_3$, haloalkyl, cycloalkyl, halogen, hydroxyalkyl, —N=CH—($R^{31}$), —C(=O)N($R^{30})_2$, —N($R^{30})_2$, —NSO$_2R^{31}$, —O$R^{30}$, —SO$_2$($R^{31}$), —SO$_2$NH$R^{30}$, —N($R^{30}$)C(=O)N($R^{30})_2$ and —N($R^{30}$)C(=O)$R^{31}$;

$R^7$ and $R^8$ are the same or different, each being independently selected from the group consisting of H, alkyl, alkylaryl, heteroaryl, hydroxyl, —CN, alkoxy, —N($R^{30})_2$, —N(H)S(O)$_2$alkyl, —N(H)C(=O)N(H)alkyl, —$(CH_2)_q$OH, —$(CH_2)_q$Oalkyl, —$(CH_2)_q$N(H)-alkyl, —$(CH_2)_q$N(H)—S(O)$_2$alkyl, and —$(CH_2)_q$N(H)—CO—N(H)alkyl; or alternatively $R^7$ and $R^8$ taken together with the carbon atom to which they are shown attached is =O, =S, =NH, =N(alkyl), =N(Oalkyl), =N(OH) or cycloalkyl;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyl, alkoxy, hydroxyalkyl, —N($R^{30})_2$, —C(=O)N($R^{30})_2$, —$(CH_2)_q$OH, —$(CH_2)_q$O$R^{31}$, —$(CH_2)_q$NH$R^3$, —$(CH_2)_q$N($R^{31})_2$, —O$R^{30}$, halogen, and —C(=O)$R^{31}$; or wherein two $R^{10}$ moieties together on the same carbon atom form =O;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, hydroxyl, alkoxy, carboxamide, —N($R^{30})_2$, CO$_2$H, —$(CH_2)_q$OH, —$(CH_2)_q$O$R^{31}$, —$(CH_2)_q$NH$R^{31}$, —$(CH_2)_q$N($R^{31})_2$, —O$R^{30}$, halogen, and —C(=O)$R^{31}$; or wherein two $R^{11}$ moieties together on the same carbon atom form =O;

$R^{12}$ is selected from the group consisting of H, alkyl, haloalkyl —CN, CF$_2$H, CF$_3$, —C(=O)N($R^{30})_2$, —$(CH_2)_q$OH, —$(CH_2)_q$O$R^{31}$, —$(CH_2)_q$NH$R^{31}$, —$(CH_2)_q$N($R^{31})_2$, and —S(O$_2$)$R^{31}$;

D is a three to nine membered cycloalkyl, three to nine membered cycloalkenyl, or a five to eight membered aryl, heteroaryl, heterocyclenyl or heterocyclyl ring having 0-4 heteroatoms or moieties independently selected from the group consisting of N, O, S and SO$_2$, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, -alkylamino, -alkylthiocarboxy, alkylheteroaryl, alkylthio, alkylsulfinyl-, —C(=O)—O-alkyl, amidinyl, aralkyl, aralkenyl, aralkoxy, aralkoxycarbonyl, aralkylthio, aryl, cyano, cycloalkyl, cycloalkenyl, guanidinyl, halogen, haloalkyl, haloalkoxy, heteroalkyl, heteroaryl, heterocyclyl, heterocyclenyl, hydroxyalkyl, hydroxamate, nitro, trifluoromethoxy, —$(CH_2)_q$OH, —$(CH_2)_q$O$R^{31}$, —$(CH_2)_q$N H$_2$, —$(CH_2)_q$NH$R^{31}$, —$(CH_2)_q$N($R^{31})_2$, —$(CH_2)_q$C(=O)NH$R^{31}$, —$(CH_2)_q$SO$_2R^{31}$, —$(CH_2)_q$NHSO$_2R^{31}$, —$(CH_2)_q$SO$_2$NH$R^{31}$, -alkynylC($R^{31})_2$O$R^{31}$, —C(=O)$R^{30}$, —C(=O)N($R^{30})_2$, —C(=N$R^{30}$)NH$R^{30}$, —C(=NOH)N($R^{30})_2$, —C(=NO$R^{31}$)N($R^{30})_2$, —C(=O)O$R^{30}$, —N($R^{30})_2$, —N($R^{30}$)C(=O)$R^{31}$, —NHC(=O)N($R^{30})_2$, —N($R^{30}$)C(=O)O$R^{31}$, —N($R^{30}$)C(=NCN)N($R^{30})_2$, —N($R^{30}$)C(=O)N($R^{30}$)SO$_2R^{31}$), —N($R^{30}$)C(=O)N($R^{30})_2$, —N($R^{30}$)SO$_2R^{31}$, —N($R^{30}$)S(O)$_2$N($R^{30})_2$, —O$R^{30}$, —OC(=O)N($R^{30})_2$, —S$R^{30}$, —SO$_2$N($R^{30})_2$, —SO$_2$($R^{31}$), —OSO$_2$($R^{31}$), and —OSi($R^{30})_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, -alkylamino, -alkylthiocarboxy, alkylheteroaryl, alkylthio, alkylsulfinyl-, —C(=O)—O-alkyl, amidinyl, aralkyl, aralkenyl, aralkoxy, aralkoxycarbonyl, aralkylthio, aryl, cyano, cycloalkyl, cycloalkenyl, guanidinyl, halogen, haloalkyl, heteroalkyl, heteroaryl, heterocyclyl, heterocyclenyl, hydroxyalkyl, hydroxamate, nitro, trifluoromethoxy, —$(CH_2)_q$OH, —$(CH_2)_q$OR$^{31}$, —$(CH_2)_q$NH$_2$, —$(CH_2)_q$NHR$^{31}$, —$(CH_2)_q$N(R$^{31}$)$_2$, —$(CH_2)_q$C(=O)NHR$^{31}$, —$(CH_2)_q$SO$_2$R$^{31}$, —$(CH_2)_q$NHSO$_2$R$^{31}$, —$(CH_2)_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —CHR$^3$C(=O)—, —(CHR$^{13}$)$_r$O—, —(CHR$^{13}$)$_r$N(R$^{30}$)—, —C(=O)—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)—$_r$C(=O)— and —(CHR$^{13}$)—$_r$N(H)C(=O)—; or alternatively Y is cycloalkyl, heterocyclenyl, or heterocyclyl wherein the cycloalkyl, heterocyclenyl, or heterocyclyl is fused with ring D;

the $R^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CHR$^{30}$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the $R^{30}$ moieties can be the same or different, each being independently selected from the group consisting of H, alkyl, alkylaryl, aryl, aralkyl, cycloalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(OH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

the $R^{31}$ moieties can be the same or different, each being independently selected from the group consisting of alkyl, alkylaryl, aryl, aralkyl, cycloalkyl, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH$_2$)$_q$NHaryl, —(CH$_2$)$_q$NHaralkyl, —(CH$_2$)$_q$NHcycloalkyl, —(CH$_2$)$_q$C(=O)NHalkyl, —(CH$_2$)$_q$C(=O)N(alkyl)$_2$, —(CH$_2$)$_q$C(=O)NHalkylaryl, —(CH$_2$)$_q$C(=O)NHaryl, —(CH$_2$)$_q$C(=O)NHaralkyl, —(CH$_2$)$_q$C(=O)NHcycloalkyl, —(CH$_2$)$_q$SO$_2$alkyl, —(CH$_2$)$_q$SO$_2$alkylaryl, —(CH$_2$)$_q$SO$_2$aryl, —(CH$_2$)$_q$SO$_2$aralkyl, —(CH$_2$)$_q$SO$_2$cycloalkyl, —(CH$_2$)$_q$NSO$_2$alkyl, —(CH$_2$)$_q$NSO$_2$alkylaryl, —(CH$_2$)$_q$NSO$_2$aryl, —(CH$_2$)$_q$NSO$_2$aralkyl, —(CH$_2$)$_q$NSO$_2$cycloalkyl, —(CH$_2$)$_q$SO$_2$NHalkyl, —(CH$_2$)$_q$SO$_2$NHalkylaryl, —(CH$_2$)$_q$SO$_2$NHaryl, —(CH$_2$)$_q$SO$_2$NHaralkyl, —(CH$_2$)$_q$SO$_2$NHcycloalkyl, heterocyclenyl, heterocyclyl, and heteroaryl;

m is 0 to 4;

n is 0 to 4;

each q can be the same or different, each being independently selected from 1 to 5; and r is 1 to 4;

with the proviso that when a nitrogen is substituted by two alkyl groups, said two alkyl groups may be optionally joined to each other to form a ring.

A further feature of the invention is a pharmaceutical composition containing as active ingredient at least one compound of Formula 1 together with at least one pharmaceutically acceptable carrier or excipient.

In another embodiment, the invention provides a method of treating a CXCR3 chemokine mediated disease in a patient in need of such treatment comprising administering to the patient a therapeutically effective amount of at least one compound of Formula 1, or a pharmaceutically acceptable salt, solvate or ester thereof.

In another embodiment, the invention provides a method of inhibiting or blocking T-cell mediated chemotaxis in a patient in need of such treatment comprising administering to the patient a therapeutically effective amount of at least one compound of Formula 1, or a pharmaceutically acceptable salt, solvate or ester thereof.

The invention also provides a method of modulating (inhibiting or promoting) an inflammatory or immune response in an individual in need of such therapy, comprising administering a therapeutically effective amount of a compound of Formula 1 or a pharmaceutically acceptable salt, solvate or ester thereof.

Also disclosed is a method of treating inflammatory bowel disease (such Crohn's disease, ulcerative colitis) in a patient in need of such treatment comprising administering to the patient a therapeutically effective amount of at least one compound of Formula 1, or a pharmaceutically acceptable salt, solvate or ester thereof.

Also disclosed is a method of treating graft rejection in a patient in need of such treatment comprising administering to the patient a therapeutically effective amount of at least one compound of Formula 1, or a pharmaceutically acceptable salt, solvate or ester thereof.

DETAILED DESCRIPTION OF THE INVENTION

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used above, and throughout the specification, the following terms, unless otherwise indicated, shall be understood to have the following meanings:

"Acyl" means an H—C(=O)—, alkyl-C(=O)—, alkenyl-C(=O)—, alkynyl-C(=O)—, cycloalkyl-C(=O)—, cycloalkenyl-C(=O)—, or cycloalkynyl-C(O)— group in which the various groups are as previously described. The bond to the parent moiety is through the carbonyl carbon atom. Preferred acyls contain a lower alkyl Non-limiting examples of suitable acyl groups include formyl, acetyl, propanoyl, 2-methylpropanoyl, butanoyl and cyclohexanoyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched The alkenyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, amino, aminosulfonyl, halo, carboxyl, carboxyalkyl (non-limiting example(s) include ester), alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$, —C(=O)N(alkyl)$_2$, —C(=O)NH(alkyl), —C(=O)N(cycloalkyl)$_2$, —C(=O)NH(cycloalkyl), —NHC(=O)alkyl, urea (e.g —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)—S(O)$_2$alkyl, —NH—S(O)$_2$aryl, —N(alkyl)—S(O)$_2$aryl, —NH—S(O)$_2$NH$_2$, —NH—S(O)$_2$NHalkyl, —NH—S(O)$_2$N(alkyl)$_2$, alkylthiocarboxy, —S(O)$_2$alkyl —S(O)$_2$aryl, —OS(O)$_2$alkyl, —OS(O)$_2$aryl, sulfonyl urea (non-limiting example(s) include NHC(=S)NHalkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched or a combination thereof, and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl$_1$ are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl )$_2$, halo, hydroxy, carboxyl, carboxyalkyl (non-limiting example(s) include ester), alkoxycarbonyl, hydroxyalkyl, carbonyl (non-limiting example(s) include ketone), —C(=O)heterocyclyl, formyl, carboxamido (i.e. amido, —C(=O)NH$_2$, —C(=O)N(alkyl)$_2$, —C(=O)NH(alkyl), —C(=O)N(cycloalkyl)$_2$, —C(=O)NH(cycloalkyl)), —NHC(=O)alkyl, amidinyl, hydrazidyl, hydroxamate, —NHC(=O)H, —NHC(=O)alkyl, urea (e.g —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e. —CO$_2$NH$_2$), —NHC(=O)Oalkyl, —CO$_2$N(alkyl)$_2$, —NHC(=O)NH—S(O)$_2$alkyl, —NHC(=O)N(alkyl)-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthio, alkylthiocarboxy, —S(O)alkyl, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylheteroaryl" means an alkyl-heteroaryl- group wherein the alkyl is as previously described and the bond to the parent moiety is through the heteroaryl group.

"Alkylamino" means an —NH$_2$ or —NH$_3$+ group in which one or more of the hydrogen atoms on the nitrogen is replaced by an alkyl group as defined above. The bond to the parent is through the nitrogen.

"Alkylaryl" means an alkyl-aryl- group in which the alkyl and aryl are as described herein. Preferred alkylaryls comprise a lower alkyl group. Non-limiting examples of suitable alkylaryl groups include o-tolyl, p-tolyl and xylyl. The bond to the parent moiety is through the aryl.

"Alkylthio" means an alkyl-S— group in which the alkyl group is as described herein. Non-limiting examples of suitable alkylthio groups include methylthio, ethylthio, i-propylthio and heptylthio. The bond to the parent moiety is through the sulfur.

"Alkylthiocarboxy" means an alkyl-S—C(=O)O— group. Preferred groups are those in which the alkyl group is lower alkyl. The bond to the parent moiety is through the carboxy.

"Alkylsulfonyl" means an alkyl-S(O)$_2$— group. Preferred groups are those in which the alkyl group is lower alkyl The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, alkoxyl, aryl, aryloxy, cycloalkyl, cycloalkenyl, cyano, heteroaryl, heterocyclyl, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, alkoxycarbonyl, hydroxyalkyl, carbonyl (non-limiting example(s) include ketone), —C(=O)heterocyclyl, carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, —NHC(=O)alkyl, urea (e.g —NH(C=O)NH$_2$), —NH(C=O)NH(alkyl), —NH(C=O)NH(alkyl)$_2$, —NH(C=O)NH(heteroaryl), —NH(C=O)NH(heterocyclyl), —S(O)$_2$alkyl, and —S(O)$_2$aryl.

"Alkoxy" means an alkyl-O— group in which the alkyl group is as previously described, Non-limiting examples of suitable alkoxy groups include methoxy, ethoxy, n-propoxy, isopropoxy, n-butoxy, heptoxy and methylhydroxy. The bond to the parent moiety is through the ether oxygen.

"Alkoxycarbonyl" means an alkyl-O—C(=O)— group. Non-limiting examples of suitable alkoxycarbonyl groups include methoxycarbonyl and ethoxycarbonyl. The bond to the parent moiety is through the carbonyl.

"Aminoalkyl" means an amine-alkyl- group in which alkyl is as previously defined. Preferred aminoalkyls contain lower alkyl. Non-limiting examples of suitable aminoalkyl groups include aminomethyl and 2-Dimethylamino-2-ethyl. The bond to the parent moiety is through the alkyl.

"Amidinyl" means —C(=NR)NHR group. The R groups are defined as H, alkyl, alkylaryl, heteroaryl, hydroxyl, alkoxy, amino, ester, —NHSO$_2$alkyl, —NHSO$_2$Aryl, —NHC(=O)NHalkyl, and —NHalkyl. The bond to the parent moiety is through the carbon.

"Aralkyl" or "arylalkyl" means an aryl-alkyl- group in which the aryl and alkyl are as previously described. Preferred aralkyls comprise a lower alkyl group attached to the aryl group. Non-limiting examples of suitable aralkyl groups include benzyl, 2-phenethyl and naphthalenylmethyl. The bond to the parent moiety is through the alkyl.

"Aralkenyl" means an aryl-alkenyl- group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aralkoxy" means an aralkyl-O— group in which the aralkyl group is as described above. The bond to the parent moiety is through the oxygen group.

"Aralkoxycarbonyl" means an aralkyl-O—C(=O)— group. Non-limiting example of a suitable aralkoxycarbonyl group is benzyloxycarbonyl. The bond to the parent moiety is through the carbonyl.

"Aroyl" means an aryl-C(=O)— group in which the aryl group is as previously described The bond to the parent moiety is through the carbonyl. Non-limiting examples of suitable groups include benzoyl and 1- and 2-naphthoyl.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Arylsulfonyl" means an aryl-S(O)$_2$— group. The bond to the parent moiety is through the sulfonyl.

"Arylsulfinyl" means an aryl-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

"Carboxyalkyl" means an alkyl-C(=O)O— group. The bond to the parent moiety is through the carboxy.

Carbamates and urea substituents refer to groups with oxygens and nitrogens respectively adjacent an amide; representative carbamate and urea substituents include the following:

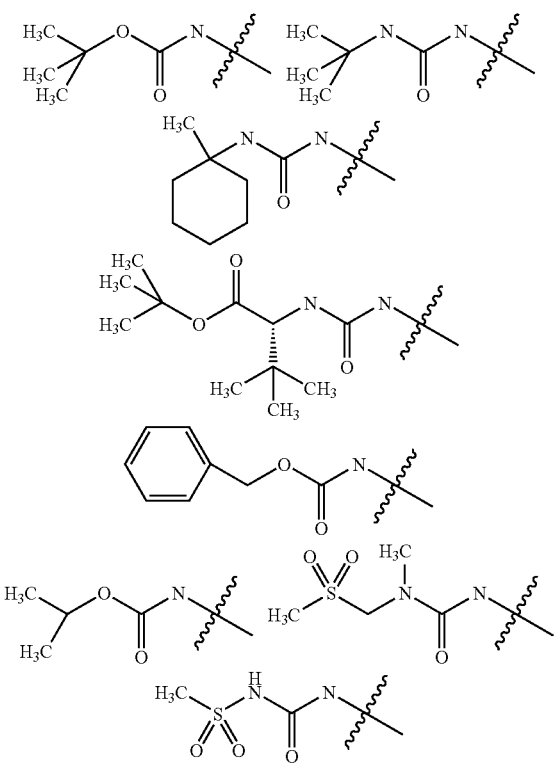

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. The term "cycloalkenyl" additionally means moieties such as cyclobutenedione, cyclopentenone, cyclopentenedione and the like.

"Halogen" (or halo) means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above. Non-limiting examples include trifluoromethyl, 2,2,2-trifluoroethyl, 2-chloropropyl and alike.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclenyl" means a partially unsaturated monocyclic or partially unsaturated multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heterocyclenyls contain about 5 to about 6 ring atoms and 1-3 double bonds. Preferred heterocyclenyls also contain at least one —C=N as part of the ring. The "heterocyclenyl" can be optionally substituted by one or more "ring system substituents" which may be the same or different, and are as defined herein. The prefix aza, oxa or thia before the heterocyclenyl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heterocyclenyls include dihydroimidazole, dihydrooxazole, dihydrooxadiazole, dihydrothiazole, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or SS-dioxide. Non-limiting examples of suitable monocyclic heterocyclyl rings include piperidyl, pyrrolidinyl, piperazinyl, morpholinyl, oxazolidinyl, imidazolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. Also included are ring systems comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Non-limiting examples of suitable monocyclic azaheterocyclic (i.e., azaheterocyclyl) groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, dihydro-2-pyrrolinyl, dihydro-3-pyrrolinyl, dihydro-2-imidazolinyl, dihydro-2-pyrazolinyl, dihydro-4,5-trizolyl and the like. Non-limiting examples of suitable oxaheterocyclic (i.e., oxaheterocyclyl) groups include 3,4-dihydro-2H-pyran, dihydrofuranyl, fluorodihydrofuranyl, and the like. Non-limiting example of a suitable multicyclic oxaheterocyclic group is 7-oxabicyclo[2.2.1]heptenyl. Non-limiting examples of suitable monocyclic thiaheterocyclic (i.e., thiaheterocyclyl) rings include dihydrothiophenyl, dihydrothiopyranyl, and the like.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-(3-yl)methyl. The bond to the parent moiety is through the alkyl.

"Heteroaralkenyl" means an heteroaryl-alkenyl- group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl. The bond to the parent moiety is through the alkyl.

"Hydroxamate" means an alkyl-C(=O)NH—O— group. The bond to the parent moiety is through the oxygen group.

"Ring system substituent" means a substituent attached to an aromatic or non-aromatic ring system which, for example, replaces an available hydrogen on the ring system. Ring system substituents may be the same or different, each being independently selected from the group consisting of H, alkyl, alkenyl, alkynyl, alkoxyl, aryl, aroyl, aryloxy, cycloalkyl, cycloalkenyl, heteroaryl, heterocyclyl, alkylaryl, alkytheteroaryl, aralkyl, aralkenyl, aralkoxy, aralkoxycarbonyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), cyano, alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, -amidino, hydrazido, hydroxamate, —NHC(=O)H, —NHC(=O)alkyl, urea (e.g —NH(C=O)NH$_2$), —NH(C=O)NH(alkyl), —NH(C=O)N(alkyl)$_2$, —NH(C=O)NH(heteroaryl), —NH(C=O)NH(heterocyclyl), guanidinyl, —NHC(=NCN)NH$_2$, —NHC(=NCN)N(alkyl)$_2$, carbamoyl (i.e. —CO$_2$NH$_2$), —NHC(=O)Oalkyl, —CO$_2$N(alkyl)$_2$, —NHC(=O)NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)—S(O)$_2$aryl, —NH—S(O)$_2$NH$_2$, —NH—S(O)$_2$NHalkyl, —NH—S(O)$_2$N(alkyl)$_2$,thio, alkylthiocarboxy, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$.

"Spiroalkyl" means an alkylene group wherein two carbon atoms of an alkyl group are attached to one carbon atom of a parent molecular group thereby forming a carbocyclic or heterocyclic ring of three to eleven atoms. Representative structures include examples such as:

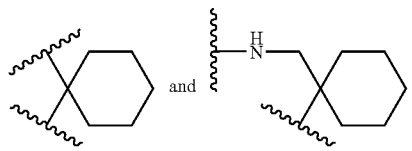

The spiroalkyl groups of this invention can be optionally substituted by one or more ring system substituents, wherein "ring system substituent" is as defined herein.

"Ring system substituent" also means a cyclic ring of 3 to 7 ring atoms of which may contain 1 or 2 heteroatoms, attached to an aryl, heteroaryl, or heterocyclyl ring by simultaneously substituting two ring hydrogen atoms on said aryl, heteroaryl, heterocyclyl ring. Non-limiting examples include:

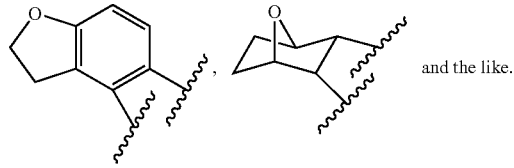

and the like.

The term "optionally substituted" means optional substitution with the specified groups, radicals or moieties, in available position or positions.

With reference to the number of moieties (non-limiting example(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line ——— as a bond generally indicates a mixture of, or either of, the possible isomers, non-limiting example(s) include, containing (R)— and (S)— stereochemistry. For example,

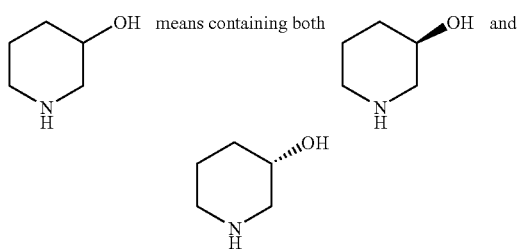

A dashed line ( ------- ) represents an optional bond.
Lines drawn into the ring systems, such as, for example:

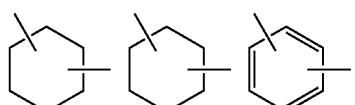

indicate that the indicated line (bond) may be attached to any of the substitutable ring atoms, non limiting examples include carbon, nitrogen and sulfur ring atoms.

As well known in the art, a bond drawn from a particular atom wherein no moiety is depicted at the terminal end of the bond indicates a methyl group bound through that bond to the atom, unless stated otherwise. For example:

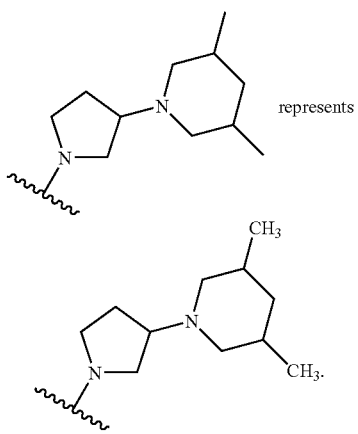

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Metabolic conjugates", for example, glucuronides and sulfates which can undergo reversible conversion to compounds of Formula 1 are contemplated in this application.

"Effective amount" or "therapeutically effective amount" is meant to describe an amount of compound or a composition of the present invention effective to antagonize CXCR3 and thus produce the desired therapeutic effect in a suitable patient.

An "inflammatory disease" is characterized by a local or systemic, acute or chronic inflammation. An "immune disease" is characterized by a hyper- or hypo-reaction of the immune system. Examples of inflammatory or immune diseases include neurodegenerative diseases (e.g., Alzheimer's disease), multiple sclerosis, systemic lupus erythematosus, rheumatoid arthritis, ankylosing spondylitis, psoriatic arthritis, juvenile rheumatoid arthritis, atherosclerosis, vasculitis, chronic heart failure, cerebrovascular ischemia, encephalitis, meningitis, hepatitis, nephritis, sepsis, sarcoidosis, psoriasis, eczema, urticaria, type I diabetes, asthma, conjunctivitis, ophthalmic inflammation, otitis, allergic rhinitis, chronic obstructive pulmonary disease, sinusitis, dermatitis, inflammatory bowel disease, ulcerative colitis, Crohn's disease, Behcet's syndrome, pulmonary fibrosis, endometriosis, gout, cancer, cachexia, viral infections, bacterial infections, organ transplant conditions, skin transplant conditions, and graft versus host diseases.

"Mammal" means humans and other mammalian animals.

"Patient" includes both human and animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$. In general, the solvated forms are equivalent to the unsolvated forms and are intended to be encompassed within the scope of this invention.

The compounds of Formula 1 form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (non-limiting example(s) include, non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331 These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulhates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (non-limiting example(s) include methyl, ethyl, propyl, and butyl chlorides, bromides and iodides), dialkyl sulfates (non-limiting example(s) include dimethyl, diethyl, dibutyl, and diamyl sulfates), long chain halides (non-limiting example(s) include decyl, lauryl, myristyl and stearyl chlorides, bromides and iodides), aralkyl halides (non-limiting example(s) include benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino), (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof or by a 2,3-di ($C_{6-24}$)acyl glycerol.

Compounds of Formula 1, and salts, solvates, esters and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate, ester and prodrug of enantiomers, stereoisomers, rotamers, tautomers, racemates or prodrugs of the inventive compounds.

It should also be noted that throughout the specification and Claims appended hereto any formula, compound, moiety or chemical illustration with unsatisfied valences is assumed to have the hydrogen atom to satisfy the valences unless the context indicates a bond.

In one embodiment, in formula 1, Z is N or NO (i.e., N-oxide).

In another embodiment, in formula 1, G is —C≡N.

In another embodiment, in formula 1, G is

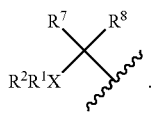

In another embodiment, G is

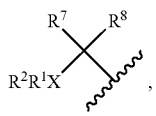

wherein X is N or O.

In another embodiment, G is

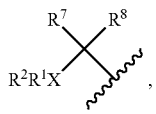

wherein $R^1$ and $R^2$ are independently absent or present, and if present each is independently selected from the group consisting of H, alkyl, hydroxyalkyl, and cycloalkyl In another embodiment, G is

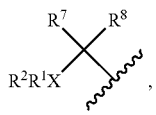

wherein $R^1$ and $R^2$ are independently absent or present, and if present each is independently selected from the group consisting of H, —$CH_3$, —$CH_2CH_3$, —$CH_2CH_2OH$, and cyclopropyl.

In another embodiment, in formula 1, $R^3$ is selected from the group consisting of H, alkyl, alkoxy, halo, and haloalkyl.

In another embodiment, in formula 1, $R^3$ is selected from the group consisting of —H, —$CH_3$, $OCH_3$, —Cl and —$CF_3$.

In another embodiment, in formula 1, wherein $R^5$ is selected from the group consisting of H, alkyl, —$OR^{30}$, —$N(R^{30})_2$, and halogen.

In another embodiment, in formula 1, wherein $R^5$ is H, $CH_3$, OH, $NH_2$, and F.

In another embodiment, in formula 1, wherein $R^5$ is H.

In another embodiment, in formula 1, $R^6$ is selected from the group consisting of H, alkyl, —$OR^{30}$, —$N(R^{30})_2$, and halogen In another embodiment, in formula 1, $R^6$ is selected from the group consisting of H, $CH_3$, OH, $NH_2$, and F.

In another embodiment, in formula 1, $R^6$ is selected from the group consisting of H and alkyl.

In another embodiment, in formula 1, $R^6$ is selected from the group consisting of —H and —$CH_3$.

In another embodiment, in formula 1, G is

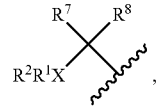

wherein $R^7$ and $R^8$ are both H, or $R^7$ and $R^8$ taken together with the carbon atom to which they are shown attached is =O.

In another embodiment, in formula 1, $R^{10}$ is selected from the group consisting of alkyl, hydroxyl, and alkoxy, or wherein two $R^{10}$ moieties together on the same carbon atom form =O, and m is 1-2.

In another embodiment, in formula 1, $R^{10}$ is alkyl, and m is 1-2.

In another embodiment, in formula 1, m is 1-2, and $R^{10}$ is selected from the group consisting of —$CH_3$ and —$CH_2CH_3$.

In another embodiment, in formula 1, $R^{11}$ is selected from the group consisting of H, alkyl, alkoxy, and hydroxyl, or wherein two $R^{11}$ moieties together on the same carbon atom form =O; and n is 1-2.

In another embodiment, in formula 1, $R^{11}$ is H and n is 1.

In another embodiment, in formula 1, $R^{12}$ is selected from the group consisting of H, alkyl, and haloalkyl.

In another embodiment, in formula 1, $R^{12}$ is H, $CH_3$, or $CF_3$.

In another embodiment, in formula 1, $R^{12}$ is H.

In another embodiment, in formula 1, Y is selected from the group consisting of: —$(CHR^{13})_r$— and —C(=O)—.

In another embodiment, in formula 1, Y is selected from the group consisting of: —$CH_2$— and —C(=O)—.

In another embodiment, in formula 1, D is 5 to 9 membered aryl optionally substituted with 1-2 $R^{20}$ moieties selected independently from the group consisting of halogen, —$OR^{30}$, alkyl, —$N(R^{30})_2$, haloalkyl, cyano, —$SO_2(R^{31})$, —$SO_2N(R^{30})_2$, and haloalkoxy.

In another embodiment, in formula 1, D is 5 to 9 membered aryl optionally substituted with 1-2 $R^{20}$ moieties selected independently from the group consisting of halogen, hydroxyl, alkyl, alkoxy, aminoalkyl, haloalkyl, cyano, sulfonylalkyl, sulfonylamino and haloalkoxy.

In another embodiment, in formula 1, D is 5 to 9 membered aryl optionally substituted with 1-2 $R^{20}$ moieties selected independently from the group consisting of halogen, alkyl, haloalkyl, and haloalkoxy. In another embodiment, in formula 1, D is 5 to 9 membered aryl optionally substituted with 1-2 $R^{20}$ moieties selected independently from the group consisting of halogen, hydroxyl, alkyl, alkoxy, aminoalkyl, haloalkyl, cyano, sulfonylalkyl, sulfonylamino and haloalkoxy.

In another embodiment, in formula 1, D is phenyl, substituted with 1-2 moieties selected independently from the group consisting of alkyl, alkoxy, —Cl, —F, and trifluoromethoxy.

In another embodiment, in formula 1,
Z is N or NO;
G is

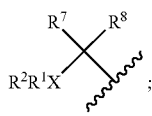

X is N or O;
$R^1$ and $R^2$ are independently absent or present, and if present each is independently selected from the group consisting of H, alkyl, aryl and cycloalkyl or alternatively when X is N, the N taken together with the $R^1$ and $R^2$ forms a cycloalkyl or a heterocyclyl;
oalkyl, heteroalkyl, heteroaryl, heterocyclyl, heterocyclenyl, hydroxyalkyl, trifluoromethoxy, —(CH$_2$)$_q$OR$^{31}$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —alkynylC(R$^{31}$)$_2$OR$^{31}$, —C(=O)R$^{30}$, —C(=O)N(R$^{30}$)$_2$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SO$_2$N(R$^{30}$)$_2$, and —SO$_2$(R$^{31}$), or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is
$R^3$, $R^5$, and $R^6$ are independently selected from the group consisting of —H, alkyl, haloalkyl, amino, aminoalkyl, alkoxy, CF$_3$, alkyl, halogen, or hydroxyl;
$R^7$ and $R^8$ are independently selected from the group consisting of H and alkyl, or $R^7$ and $R^8$ taken together with the carbon atom to which they are shown attached is =O;
$R^{10}$ and $R^{11}$ are independently selected from the group consisting of H, alkyl, —N(R$^{30}$)$_2$, halogen, or hydroxyl or wherein two $R^{10}$ or $R^{11}$ moieties together on the same carbon atom form =O;
$R^{12}$ is selected from the group consisting of H, alkyl, haloalkyl, and CF$_3$;
Y is selected from the group consisting of —(CR$^{13}$R$^{13}$)—, —CHR$^{13}$C(=O)—, —(CHR$^{13}$)O—, —(CHR$^{13}$)N(R$^{30}$)—, —C(=O)—, CH-heteroaryl-, —(CHR$^{13}$)C(=O)— and —(CHR$^{13}$)$_r$N(H)C(=O)—.

the $R^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —C(=O)R$^{30}$, —C(=O)N(R$^{30}$)$_2$, —(CHR$^{30}$)$_q$OR$^{31}$, —(CHR$^{30}$)$_q$OR$^{31}$, and —(CH$^2$)$_q$(=O)NHR$^{31}$;

the $R^{30}$ and $R^{31}$ moieties can be the same or different, each being independently selected from the group consisting of H, alkyl, alkylaryl, aryl, aralkyl, cycloalkyl, heterocyclenyl, heterocyclyl, and heteroaryl, D is a three to nine membered cycloalkyl, three to nine membered cycloalkenyl; or a five to eight membered aryl, heteroaryl, heterocyclenyl or heterocyclyl ring having 0-4 heteroatoms independently selected from N, O, S or, SO$_2$, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, -alkylamino, -alkylthiocarboxy, alkylheteroaryl, alkylthio, alkylsulfinyl-, —C(=O)—O-alkyl, amidinyl, aralkyl, aralkenyl, aralkoxy, aralkoxycarbonyl, aralkylthio, aryl, cyano, cycloalkyl, cycloalkenyl, guanidinyl, halogen, haloalkyl, haloalkoxy, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$, or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties; and m and n are independently an integer from 1 to 4.

In another embodiment, in formula 1,
Z is N;
G is

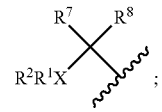

X is N;
$R^1$ and $R^2$ are independently absent or present, and if present each is independently selected from the group consisting of H, alkyl, and cycloalkyl, or alternatively when X is N, the N taken together with the $R^1$ and $R^2$ forms a cycloalkyl or a heterocyclyl;

$R^3$, $R^5$, and $R^6$ are independently selected from the group consisting of —H, alkyl, haloalkyl, amino, aminoalkyl, alkoxy, CF$_3$, halogen, and hydroxyl;

$R^7$ and $R^8$ taken together with the carbon atom to which they are shown attached is =O, $R^{10}$, $R^{11}$ are independently selected from the group consisting of H, alkyl) —N(R$^{30}$)$_2$, halogen, or hydroxyl or wherein two $R^{10}$ or $R^{11}$ moieties together on the same carbon atom form =O;

$R^{12}$ is selected from the group consisting of H, alkyl, haloalkyl, and CF$_3$;

Y is selected from the group consisting of —(CR$^{13}$R$^{13}$)—, —CHR$^{13}$C(=O)— or —C(=O)—;

the $R^{13}$ moieties can be the same or different, each being independently selected from the group consisting of H, alkyl, alkylaryl, cycloalkyl, alkoxy, aryl, heteroaryl, heterocyclenyl, heterocyclyl, or spiroalkyl;

the $R^{30}$ and $R^{31}$ moieties can be the same or different, each being independently selected from the group consisting of H, alkyl, alkylaryl, aryl, aralkyl, cycloalkyl, heterocyclenyl, heterocyclyl, and heteroaryl;

D is a phenyl or a five to eight membered aryl, heteroaryl, heterocyclenyl or a heterocyclyl ring having 0-4 heteroatoms independently selected from N, O, S or, $SO_2$, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, -alkylamino, -alkylthiocarboxy, alkylheteroaryl, alkylthio, alkylsulfinyl-, —C(=O)—O—alkyl, amidinyl, aralkyl, aralkenyl, aralkoxy, aralkoxycarbonyl, aralkylthio, aryl, cyano, cycloalkyl, cycloalkenyl, guanidinyl, halogen, haloalkyl, haloalkoxy, heteroalkyl, heteroaryl, heterocyclyl, heterocyclenyl, hydroxyalkyl, hydroxamate, nitro, trifluoromethoxy, —$(CH_2)_q$OH, —$(CH_2)_q$OR$^{31}$, —$(CH_2)_q$NH$_2$, —$(CH_2)_q$NHR$^{31}$, —$(CH_2)_q$N(R$^{31}$)$_2$, —$(CH_2)_q$C(=O)NHR$^{31}$, —$(CH_2)_q$SO$_2$R$^{31}$, —$(CH_2)_q$NHSO$_2$R$^{31}$, —$(CH_2)_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$) and —OSi(R$^{30}$)$_3$, or alternatively two $R^{20}$ moieties are linked together to form a five or six membered aryl; cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties; and m and n are independently an integer from 1 to 4.

In another embodiment, in formula 1,
Z is N;
G is

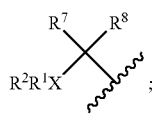

X is N;

$R^1$ and $R^2$ are independently absent or present, and if present each is independently selected from the group consisting of H, alkyl, and cycloalkyl, or alternatively when X is N, the N taken together with the $R^1$ and $R^2$ forms a cycloalkyl or a heterocyclyl;

$R^3$, $R^5$, and $R^6$ are independently selected from the group consisting of —H, alkyl, haloalkyl, amino, aminoalkyl, alkoxy, $CF_3$, halogen, and hydroxyl;

$R^7$ and $R^8$ taken together with the carbon atom to which they are shown attached is =O;

$R^{10}$, $R^{11}$ are independently selected from the group consisting of H, alkyl, amino, amino alkyl, halogen, or hydroxyl or wherein two $R^{10}$ or $R^{11}$ moieties together on the same carbon atom form =O;

$R^{12}$ is selected from the group consisting of H, alkyl, haloalkyl, and $CF_3$;

Y is selected from the group consisting of —(CR$^{13}$R$^{13}$)—, —CHR$^{13}$C(=O)— or —C(=O)—;

the $R^{13}$ moieties can be the same or different, each being independently selected from the group consisting of H, alkyl, alkoxy or cycloalkyl.

D is a phenyl or a five to eight membered aryl, heteroaryl, heterocyclenyl or a heterocyclyl ring having 0-4 heteroatoms independently selected from N, O, S or, $SO_2$, wherein ring D is unsubstituted or optionally substituted with 1-5 independently selected $R^{20}$ Moieties;

the $R^{20}$ moieties can be the same or different, each being independently selected from the group consisting of H, alkyl, alkenyl, alkoxy, cycloalkyl, cycloalkenyl, amino, aminoalkyl, aminocarboxyalkyl, aminosulfonylalkyl, carboxylaminoalkyl, acetyl, cyano, halogen, haloalkyl, hydroxyl, heterocyclyl, hydroxyalkyl, sulfonylmethyl, sulfonylamino, trifluoromethoxyl, or alternatively two $R^{20}$ moieties are linked together to form a five or six membered aryl, cycloalkyl, heterocyclyl, heterocyclenyl, or heteroaryl ring; and m and n are independently an integer from 1 to 4.

In another embodiment, in formula 1,
Z is N;
G is

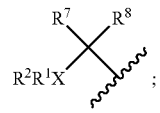

X is N or O;

$R^1$ and $R^2$ are independently absent or present, and if present each is independently selected from the group consisting of H, —$CH_3$, —$CH_2CH_3$, cyclopropyl and alkyl;

$R^3$, $R^5$, $R^6$ is independently selected from the group consisting of H, —$CH_3$, —F, —Cl, —OH, —$OCH_3$, —$OCF_3$, $NH_2$, $SO_2CH_3$, and —$CF_3$;

$R^7$ and $R^8$ are both H, or $R^7$ and $R^8$ taken together with the carbon atom to which they are shown attached is =O;

$R^{10}$ is selected from the group consisting of —$CH_3$, —$CH_2CH_3$, and hydroxyl, or two $R^{10}$ moieties together on the same carbon atom form =O, and m is 1-2;

$R^{11}$ is selected from the group consisting of H and hydroxyl or two $R^{11}$ moieties together on the same carbon atom form =O, and n is 1;

$R^{12}$ is selected from the group consisting of H and $CF_3$;

Y is selected from the group consisting of —$CH_2$— and —C(=O)—, and

D is a phenyl, or a 6 membered heteroaryl having 0-2 heteroatoms independently selected from N, O, S or, $SO_2$ wherein ring D is substituted with 1-2 moieties selected independently from the group consisting of —Cl, —$CH_3$, —C(=O)$CH_3$, —C(=O)$NH_2$, —F, —OH, $OCH_3$, $OCF_3$, $NH_2$, $NH(CH_3)_2$, $NHSO_2CH_3$, $SO_2CH_3$, $SO_2NH_2$, and trifluoromethyl.

In another embodiment, in formula 1,
Z is N;
G is

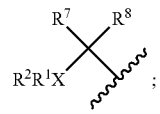

X is N or O;

$R^1$ and $R^2$ are independently absent or present, and if present each is independently selected from the group consisting of H, —$CH_3$, —$CH_2CH_3$, cyclopropyl and alkyl;

$R^3$, $R^5$, $R^6$ is independently selected from the group consisting of H, —$CH_3$, —F, —Cl, —OH, —$OCH_3$, —$OCF_3$, $NH_2$, $SO_2CH_3$, and —$CF_3$;

$R^7$ and $R^8$ are both H, or $R^7$ and $R^8$ taken together with the carbon atom to which they are shown attached is =O;

$R^{10}$ is selected from the group consisting of —$CH_3$, —$CH_2CH_3$, and hydroxyl, or two $R^{10}$ moieties together on the same carbon atom form =O, and m is 1-2;

$R^{11}$ is selected from the group consisting of H and hydroxyl or two $R^{11}$ moieties together on the same carbon atom form =O, and n is 1;

$R^{12}$ is selected from the group consisting of H and $CF_3$;

Y is selected from the group consisting of —$CH_2$— and —C(=O)—; and

D is a phenyl, or a 6 membered heteroaryl having 0-2 heteroatoms independently selected from N, O, S or, $SO_2$ wherein ring D is substituted with 1-2 moieties selected independently from the group consisting of —Cl, —$CH_3$, —C(=O)$CH_3$, —C(=O)$NH_2$, —F, —OH, $OCH_3$, $OCF_3$, $NH_2$, $NH(CH_3)_2$, $NHSO_2CH_3$, $SO_2CH_3$, $SO_2NH_2$, and trifluoromethyl.

In another embodiment, in formula 1:

Z is N or NO;

G is —C≡N, or

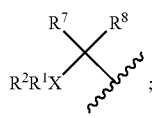

X is N or O;

$R^1$ and $R^2$ are independently absent or present, and if present each is independently selected from the group consisting of H, —$CH_3$, —$CH_2CH_3$, cyclopropyl and alkyl;

$R^3$, $R^5$, $R^6$ is independently selected from the group consisting of H, —$CH_3$, —F, —Cl, —OH, —$OCH_3$, —$OCF_3$, $SO_2CH_3$, and —$CF_3$;

$R^7$ and $R^8$ are both H, or $R^7$ and $R^8$ taken together with the carbon atom to which they are shown attached is =O;

$R^{10}$ is selected from the group consisting of —$CH_3$, —$CH_2CH_3$, and hydroxyl, or two $R^{10}$ moieties together on the same carbon atom form =O, and m is 1-2;

$R^{11}$ is selected from the group consisting of H and hydroxyl or two $R^{11}$ moieties together on the same carbon atom form =O, and n is 1;

$R^{12}$ is selected from the group consisting of H and $CF_3$;

Y is selected from the group consisting of —$CH_2$— and —C(=O)—; and

D is a phenyl, or a 6 membered heteroaryl having 0-2 heteroatoms independently selected from N, O, S or, $SO_2$ wherein ring D is substituted with 1-2 moieties selected independently from the group consisting of —Cl, —$CH_3$, —F, —OH, $NH_2$, $SO_2CH_3$, and trifluoromethoxy.

In another embodiment, the compound of formula 1 is in optically pure form.

In another embodiment, the compound of formula 1 is selected from the group consisting of

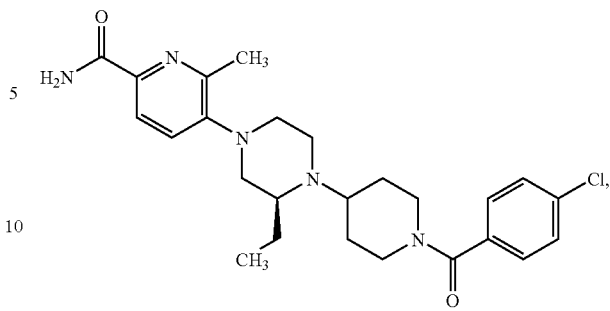

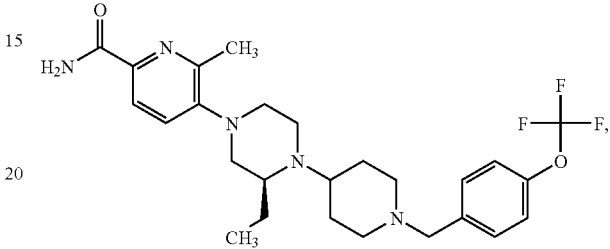

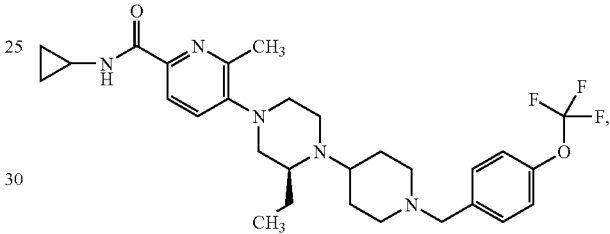

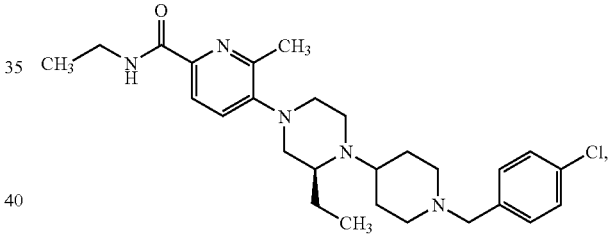

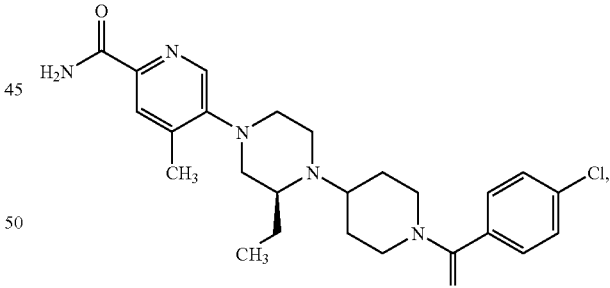

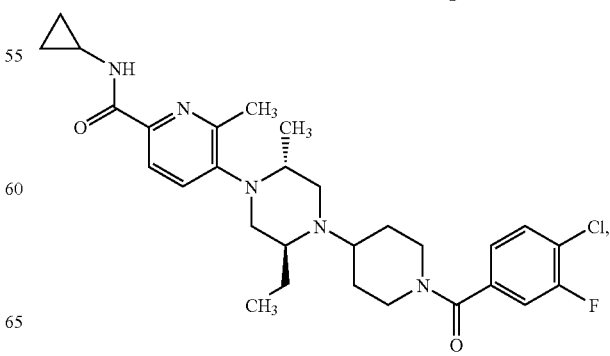

-continued

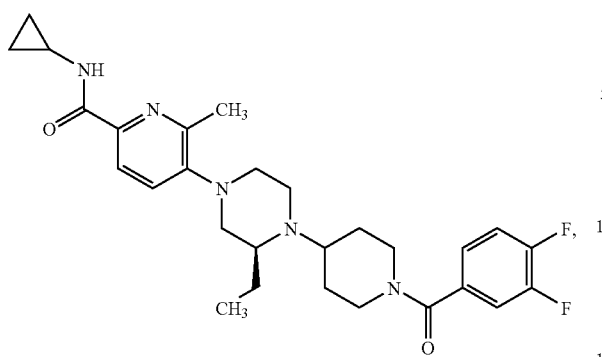
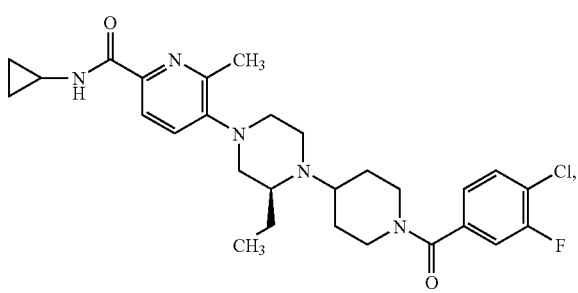
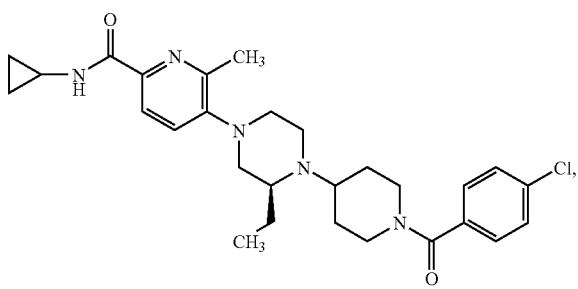
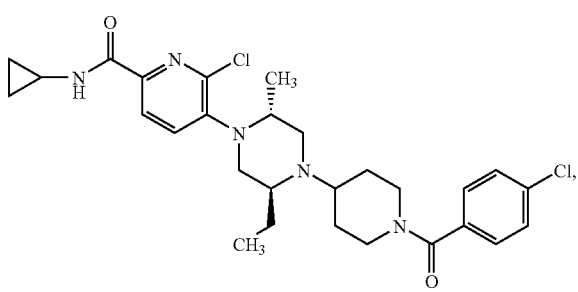
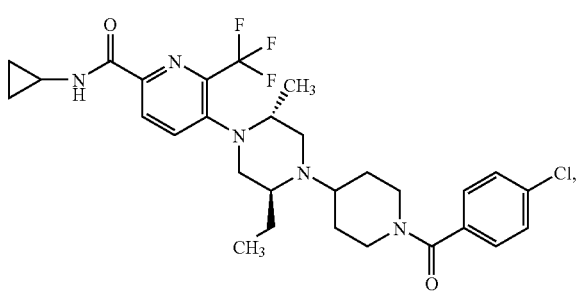

-continued

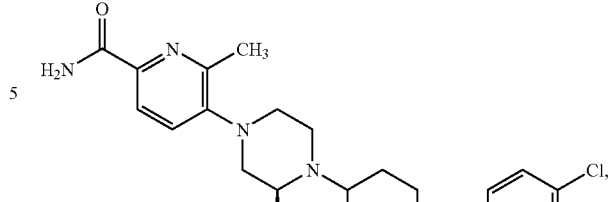
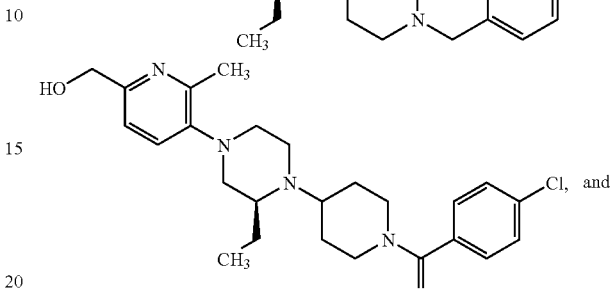
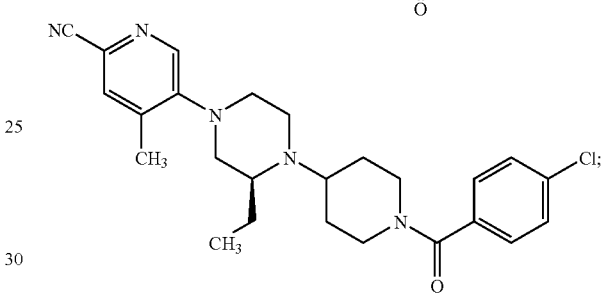

or a pharmaceutically acceptable salt, solvate, or hydrate thereof.

In yet another aspect, the compound of Formula 1 can be in purified form.

In another embodiment, the pharmaceutical composition comprising at least one compound of Formula 1, or a pharmaceutically acceptable salt, solvate or ester thereof in combination with at least one pharmaceutically acceptable carrier, further comprises at least one additional agent, drug, medicament, antibody and/or inhibitor for treating a CXCR3 chemokine receptor mediated disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In yet another embodiment, the present invention discloses methods for preparing pharmaceutical compositions comprising the inventive heterocyclic substituted piperazine compounds of Formula 1 as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato, and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients Gan include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention. Certain compounds of the present invention may exist in multiple crystalline forms or amorphous forms. All physical forms of the current invention are contemplated.

Compounds of this invention which contain unnatural proportions of atomic isotopes (i.e. "radiolabeled compounds") whether their use is therapeutic, diagnostic or as a research reagent are contemplated under this invention, Another embodiment of the invention provides a pharmaceutical composition which in addition to comprising at least one compound of formula 1, or a pharmaceutically acceptable carrier as set forth above further comprises at least one additional agent, drug, medicament, antibody and/or inhibitor for treating a CXCR3 chemokine receptor mediated disease.

In another embodiment, the CXCR3 chemokine receptor mediated disease of this invention is an inflammatory or immune disease, said inflammatory or immune disease selected from the group consisting of: neurodegenerative disease, multiple sclerosis, systemic lupus erythematosus, rheumatoid arthritis, ankylosing spondylitis, psoriatic arthritis, juvenile rheumatoid arthritis, atherosclerosis, vasculitis, chronic heart failure, cerebrovascular ischemia, encephalitis, meningitis, hepatitis, nephritis, sepsis, sarcoidosis, psoriasis, eczema, urticaria, type I diabetes, asthma, conjunctivitis, ophthalmic inflammation, otitis, allergic rhinitis, chronic obstructive pulmonary disease, sinusitis, dermatitis, inflammatory bowel disease, ulcerative colitis, Crohn's disease, Behcet's syndrome, pulmonary fibrosis, endometriosis, gout, cancer, cachexia, a viral infection, a bacterial infection, an organ transplant condition, a skin transplant condition, and a graft versus host disease.

In another embodiment, the neurodegenerative disease of this invention is Alzheimer's disease.

In another embodiment, the present invention discloses a method for treating a CXCR3 chemokine receptor mediated disease in a patient in need of such treatment comprising administering to the patient (a) an effective amount of at least one compound according to Formula 1, or a pharmaceutically acceptable salt, solvate or ester thereof concurrently or sequentially with (b) at least one additional agent, drug, medicament, antibody and/or inhibitor for treating a CXCR3 chemokine receptor mediated disease, in combination with a pharmaceutically acceptable carrier.

In another embodiment, at least one compound of Formula 1 binds to a CXCR3 receptor.

In another embodiment, the invention provides methods of preparing compounds of Formula 1, as well as methods for treating diseases, for example, treatment (e.g., palliative therapy, curative therapy, prophylactic therapy) of certain diseases and conditions e.g., inflammatory diseases (e.g., psoriasis, inflammatory bowel disease), autoimmune diseases (e.g., rheumatoid arthritis, multiple sclerosis), graft rejection (e.g., allograft rejection, xenograft rejection), ophthalmic inflammation or dry eye, infectious diseases as well as cancers and tumors, fixed drug eruptions, cutaneous delayed-type hypersensitivity responses, ophthalmic inflammation or dry eye, type I diabetes, viral meningitis and tuberculoid leprosy, comprising administering a therapeutically effective amount of a compound of Formula 1 or a pharmaceutically acceptable salt, solvate or ester thereof.

In another embodiment, the present invention provides a method for treating a CXCR3 chemokine receptor mediated disease comprising administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, corticosteroids, other chemokine inhibitors (such as CCR2 and CCR5), CB2-selective inhibitors, p38 inhibitors, biological response modifiers, anti-inflammatory agents and therapeutics.

In another embodiment, the present invention provides a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-1 2 compounds, corticosteroids, glucocorticoids, T-cell receptor directed therapies (such as anti-CD3 antibodies), immunosuppresives, methotrexate, azathioprine, and 6-mercaptopurines.

In another embodiment, the present invention provides a method of treating graft rejection in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

In another embodiment, the present invention provides a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA-4 inhibitors, FTY720, anti-IL-12 inhibitors, and CB2-selective inhibitors.

In another embodiment, the present invention provides a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

In another embodiment, the present invention provides a method of treating rheumatoid arthritis in a patient in need of such treatment the method comprising administering to the patient a therapeutically effective amount of: (a) at least one compound of Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

In another embodiment, the present invention provides a method of treating psoriasis in a patient in need of such treatment the method comprising administering to the patient a therapeutically effective amount of: a) at least one compound of Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

In another embodiment, the present invention provides a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

The invention also provides a method of treating an inflammatory or immune disease, said disease selected from the group consisting of: neurodegenerative disease, multiple sclerosis, systemic lupus erythematosus, rheumatoid arthritis, ankylosing spondylitis, psoriatic arthritis, juvenile rheumatoid arthritis, atherosclerosis, vasculitis, chronic heart failure, cerebrovascular ischemia, encephalitis, meningitis, hepatitis, nephritis, sepsis, sarcoidosis, psoriasis, eczema, urticaria, type I diabetes, asthma, conjunctivitis, ophthalmic inflammation, otitis, allergic rhinitis, chronic obstructive pulmonary disease, sinusitis, dermatitis, inflammatory bowel disease, ulcerative colitis, Crohn's disease, Behcet's syndrome, pulmonary fibrosis, endometriosis, gout, cancer, cachexia, a viral infection, a bacterial infection, an organ transplant condition, a skin transplant condition, and a graft versus host disease in a patient in need of such treatment, said method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, TNF-alpha-convertase inhibitors, cytokine inhibitors, MMP inhibitors, corticosteroids, glucocorticoids, chemokine inhibitors, CB2-selective inhibitors, biological response modifiers; anti-inflammatory agents and therapeutics.

Some specific compounds of the present invention are shown in Table 1 below, along with their $IC_{50}$ ratings. The $IC_{50}$ values are rated, "A" for $ICO_{50}$ values less than about 25 nanomolar (nM), "B" for $IC_{50}$ values in the range of from about 25 to about 100 nM and "C" for IC50 values greater than about 100 nM. For example, Compound No. 107 has an $IC_{50}$ of 0.2 nM.

TABLE 1
| Compound Number | STRUCTURE | Ki |
|---|---|---|
| 1 | 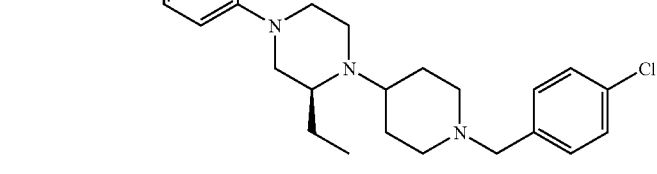 | A |
| 2 | 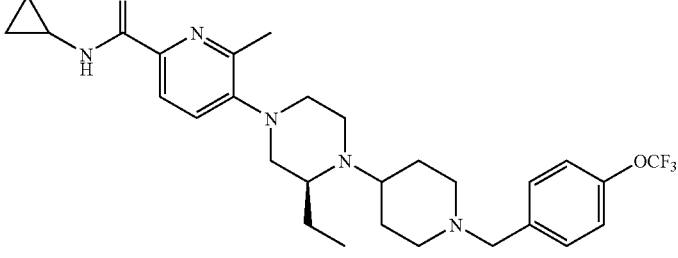 | A |
| 3 | 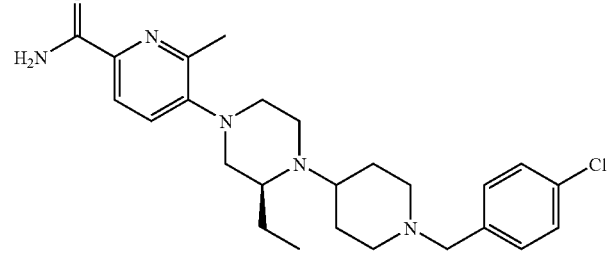 | A |
| 4 | 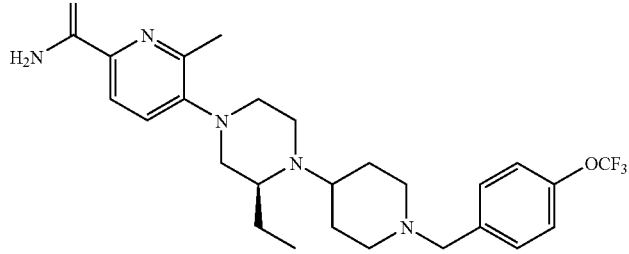 | A |
| 5 | 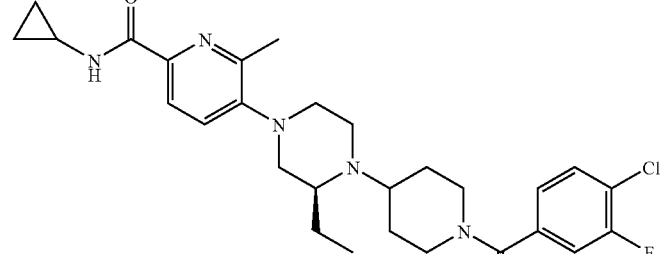 | A |

TABLE 1-continued
| Compound Number | STRUCTURE | Ki |
|---|---|---|
| 6 | 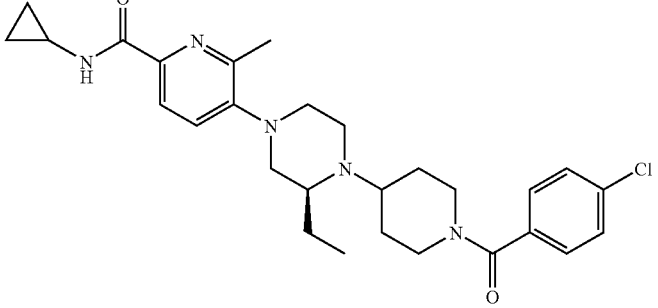 | A |
| 7 | 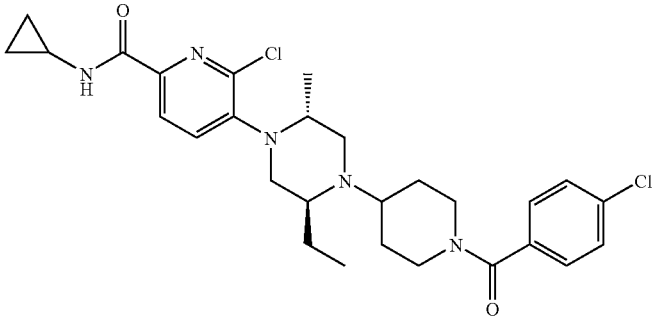 | A |
| 8 | 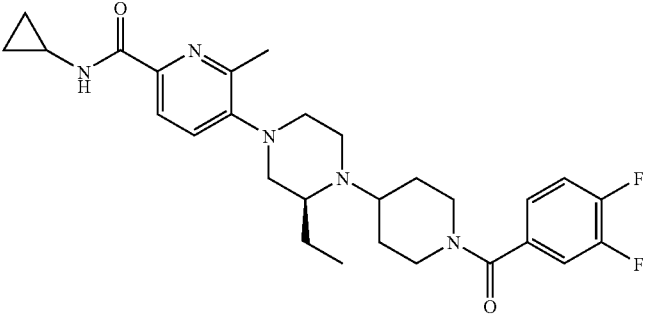 | A |
| 9 | 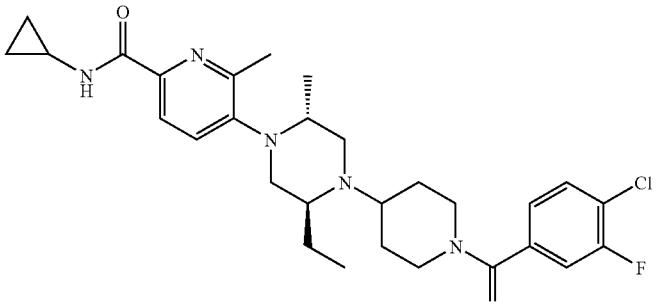 | A |

TABLE 1-continued

| Compound Number | STRUCTURE | Ki |
|---|---|---|
| 10 | 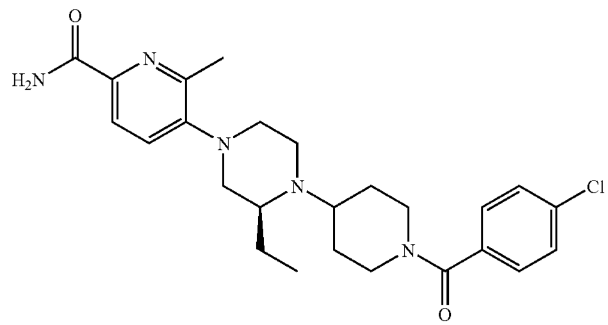 | A |
| 11 | 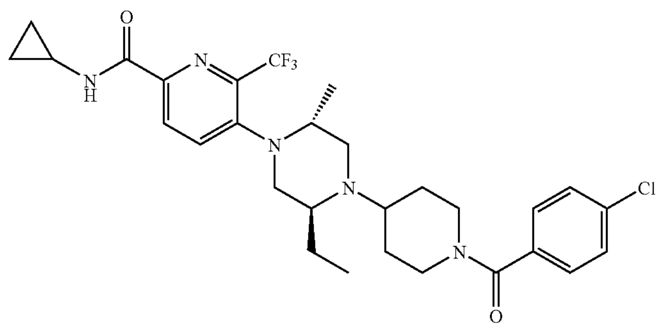 | B |
| 12 | 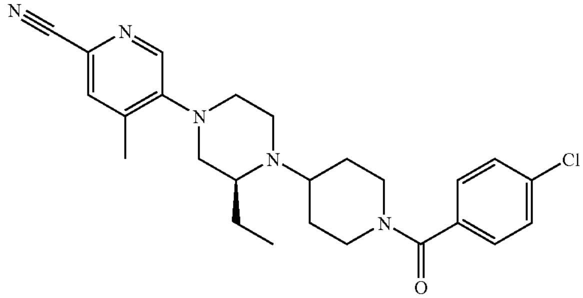 | C |
| 13 | 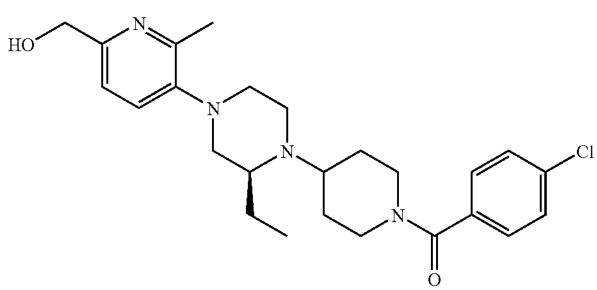 | C |
| 14 | 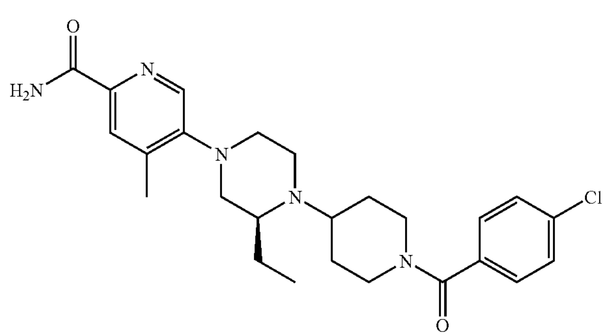 | C |

Unless otherwise stated, the following abbreviations have the stated meanings in the Examples below:
BINAP=racemic-2,2'-bis(diphenylphosphino)-1,1'-binaphthyl
DBU=1,8-diazabicyclo[5.4.0]undec-7-ene
DBN=1,5-diazabicyclo[4.3.0]non-5-ene
EDCI=1-(3-dimethylaminopropyl)-3-ethylcarbodiimide
HATU=N-(Diethylamino)-1H-1,2,3-triazolo[4,5-b-pyridine-1-ymethylene]-N-methylmethanaminium Hexafluorophosphate N-oxide
HOBT=1-hydroxybenzotriazole
DCCG dicyclohexylcarbodiimide
Dibal-H-=diisobutylaluminum hydride
DBPD=2-(Di4-butylphosphinobiphenyl
DMF=dimethylformamide
DCM=dichloromethane
LAH=lithium aluminum hydride
$NaBH(OAc)_3$=sodium triacetoxyborohydride
$NaBH_4$=sodium borohydride
$NaBH_3CN$=sodium cyanoborohydride
LDA=lithium diusopropylamide
p-TsOH=p-toluenesulfonic acid
p-TsCl=p-toluenesulfonyl chloride
PPTS=pyridinium p-toluenesulfonate
m-CPBA=m-Chloroperbenzoic acid
TMAD-N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar Ki=Dissociation Constant for substrate/receptor complex
pA2=−$logEC_{50}$, as defined by J. Hey, *Eur. J. Pharmacol.*, (1995), Vol, 294, 329-335.
Ci/mmol=Curie/mmol (a measure of specific activity)
Tr=Triphenylmethyl
Tris=Tris (hydroxymethyl)aminomethane
THF=Tetrahydrofuran
TFA=Trifluoroacetic acid

GENERAL SYNTHESIS

Compounds of the present invention can be prepared by a number of methods evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps may be varied to avoid functional group incompatibilities. One skilled in the art will recognize that a more convergent route (i.e. non-linear or preassembly of certain portions of the molecule) is a more efficient method of assembly of the target compounds. Methods for the preparation of compounds of Formula 1 were variables [$R^1, R^3, R^5, R^6, R^7, R^8, R^{10}, R^{11}, R^{12}, R^{20}, R^{21}$, A, E, L, Q, X, Y, Z, m, n, o, w and p] are as defined above, are shown in Schemes 1-4. EN is described below and $Pr^1$, $Pr^2$, $Pr^3$ and $Pr^5$ are protecting groups exemplified below.

The thus prepared compounds may be analyzed for their composition and purity as well as characterized by standard analytical techniques such as, for example, elemental analysis, NMR, mass spectroscopy, and IR spectra.

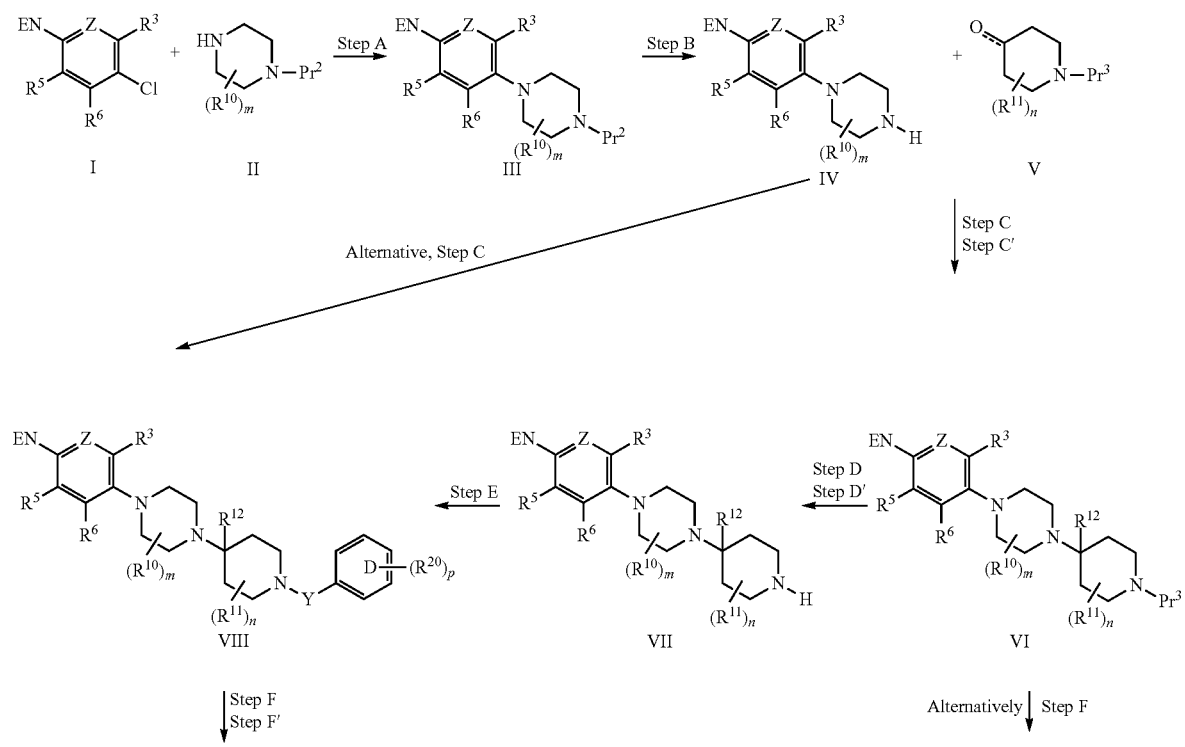

Scheme 1

-continued

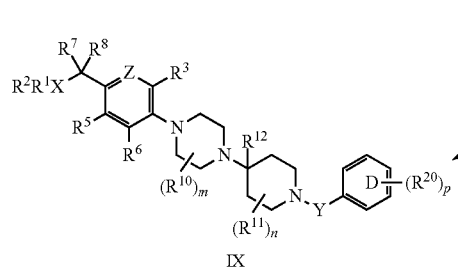
IX

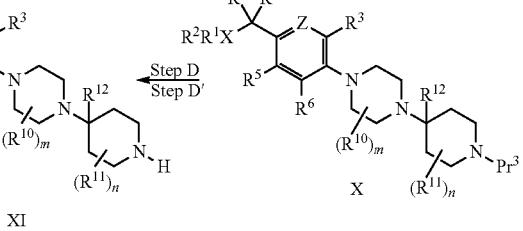
XI

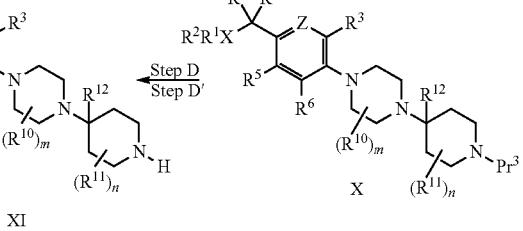
X

Step E ← Step D / Step D′ →

Alternatively,

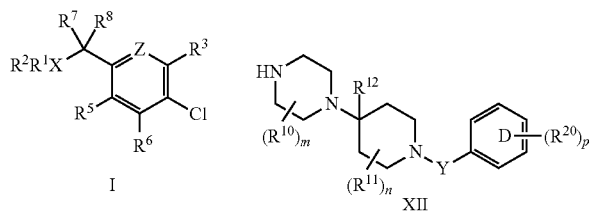
I    XII

Step A →

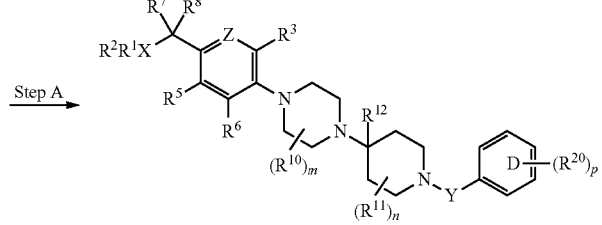
VIII

EN = Pr¹O(C═O), CN, Br, Cl H, OH, CH₃

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

One skilled in the art will recognize that the synthesis of compounds of Formula 1 may require the need for the protection of certain functional groups (i.e. derivatization for the purpose of chemical compatibility with a particular reaction condition). Suitable protecting groups for carboxylic acids include methyl, ethyl, isopropyl, or benzyl ester and the like. Suitable protecting groups for an amine ($Pr^2$ or $Pr^3$) include methyl, benzyl, ethoxyethyl, t-butoxycarbonyl, phthaloyl and the like. All protecting groups can be appended to and removed by literature methods known to those skilled in the art.

One skilled in the art will recognize that the synthesis of compounds of Formula 1 may require the construction of an amide bond. Methods include but are not limited to the use of a reactive carboxy derivative (e.g. acid halide, or ester at elevated temperatures) or the use of an acid with a coupling reagent (e.g. DECI, DCC) with an amine at 0° C. to 100° C. Suitable solvents for the reaction are halogenated hydrocarbons, ethereal solvents, dimethylformamide and the like. The reaction may be conducted under pressure or in a sealed vessel.

One skilled in the art will recognize that the synthesis of compounds of Formula 1 may require the construction of an amine bond. One such method is but not limited to the reaction of a primary or secondary amine with a reactive carbonyl (e.g. aldehyde or ketone) under reductive amination conditions. Suitable reducing reagents of the intermediate imine are sodium borohydride, sodium triacetoxyborohydride and the like at 0° C. to 100° C. Suitable solvents for the reaction are halogenated hydrocarbons, ethereal solvents, dimethylformamide and the like. Another such method is but not limited to the reaction of a primary or secondary amine with a reactive alkylating agent such as an alkyl halide, benzyl halide, mesylate, tosylate or the like. Suitable solvents for the reaction are halogenated hydrocarbons, ethereal solvents, dimethylformamide and the like. The reaction may be conducted under pressure or in a sealed vessel at 0° C. to 100° C.

One skilled in the art will recognize that the synthesis of compounds of Formula 1 may require the reduction of a reducible functional group. Suitable reducing reagents include sodium borohydride, lithium aluminum hydride, diborane and the like at −20° C. to 100° C. Suitable solvents for the reaction are halogenated hydrocarbons, ethereal solvents, dimethylformamide and the like.

One skilled in the art will recognize that the synthesis of compounds of Formula 1 may require the oxidation of a functional group. Suitable oxidizing reagents include oxygen, hydrogen peroxide, m-chloroperoxybenzoic acid and the like at −20° C. to 100° C. Suitable solvents for the reaction are halogenated hydrocarbons, ethereal solvents, water and the like.

The starting materials and the intermediates of a reaction may be isolated and purified if desired using conventional techniques, including but not limited to filtration, distillation, crystallization, chromatography and the like. Such materials can be characterized using conventional means, including physical constants and spectral data.

General Description

Step A. Amination of a Pyridine Ring

A suitably protected 2-halo pyridine or phenyl of structure I is reacted with a piperazine of structure II to form a compound of general structure III. Preferably the reaction is carried out in a solvent such as dioxane or DMF in the presence of a base such as potassium carbonate or cesium carbonate with or without the assistance of a catalyst such as palladium acetate. Alternatively, other leaving groups may replace the chlorine (O-mesyl, Br etc.) or a group capable of activation under the reaction conditions (H, OH, etc.) may be used.

Alternatively, a compound of structure I can be reacted with a compound of structure XII to form a compound of structure VIII.

Step B.

Optionally, if the product of step A is a protected piperazine of structure III, deprotection is required. When $Pr^2$ is benzyl or substituted benzyl, deprotection can be effected by reaction under a pressure of hydrogen gas in the presence of a catalyst such as palladium. When Pr² is ethoxyethyl deprotection can be effected by reaction with trimethylsilyl iodide. When Pr² is t-butoxycarbonyl deprotection can be effected with a strong acid such as trifluoroacetic acid, hydrogen chloride, p-toluenesulfonic acid.

Step C.

A piperazine of structure IV is reacted with a ketone of structure V in the presence of a reducing agent to form a compound of structure VI where $R^{12}$ is hydrogen. General conditions for the reductive amination reaction are described above.

In certain cases Pr³ represents an appropriately substituted piperidone-Y-ring D residue.

Step C' (when $R^{12}$=CN)

A piperazine of structure IV is reacted with a ketone of structure V in the presence of a reducing agent to form a compound of structure VI where $R^{12}$ is a cyanide residue. Typical conditions are the reaction of an equi-molar quantity of a piperazine of structure IV and a ketone of structure in the presence of titanium isopropoxide in a halogenated solvent such as methylene chloride for 1-48 hours. Subsequent addition of a cyanide source such as dimethylaluminum cyanide affords a compound of structure VI where $R^{12}$ is a cyanide residue.

Step D

A protected piperidine of structure VI or structure X is deprotected to provide the secondary amine of structure VII or structure XI. When Pr² is benzyl or substituted benzyl deprotection can be effected by reaction under a pressure of hydrogen gas in the presence of a catalyst such as palladium. When Pr² is ethoxyethyl deprotection can be effected by reaction with trimethylsilyl iodide. When Pr² is t-butoxycarbonyl deprotection can be effected with a strong acid such as trifluoroacetic acid.

Step D'

Optionally, functional group introduction or manipulation can be performed as required. A compound of structure VI or structure X, when $R^3$=Cl or Br is reacted with a organometallic alkylating agent such a alkylboronic acid, or an alkyl halide in the presence of a metal to promote heterocoupling, or nucleophile to yield a different structure of general structure VII or structure XI where the halogen at the $R^3$ position has been replaced by the appropriate group described for $R^3$.

Step E

A secondary piperidine of structure VII or XI is functionalized with ring D by methods such as alkylation or acylation to provide compounds of structure VIII or IX. General methods for such alkyations and acylations are described above and are well known to those skilled in the art.

Step F

Step F'

Optionally, functional group manipulation of a compound of structure IX may be done to provide additional related compounds of structure IX.

Compounds of structure IX can be prepared by the general methods outlined in scheme 1. Synthesis of the specifically exemplified compounds, were prepared as described in detailed below. The following EXAMPLES are being provided to further illustrate the present invention. They are for illustrative purposes only; the scope of the invention is not to be considered limited in any way thereby.

The following examples are intended to illustrate, but not to limit, the scope of the invention.

EXAMPLE 1

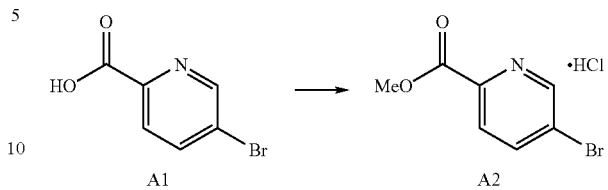

To a cooled (−78° C.) 1000 ml RB flask containing 200 ml of methanol was added thionyl chloride (10 ml, 140 mmol) dropwise followed by 5-bromopicolinic acid (15 g, 75 mmol). After stirring 10 min at −78° C., the reaction was allowed to warm to rt and stirred for 16 hr. Excess thionyl chloride and methanol were removed in vacuo to yield A2 (18 g, 95%) as a light brown solid. M+H=216

EXAMPLE 2

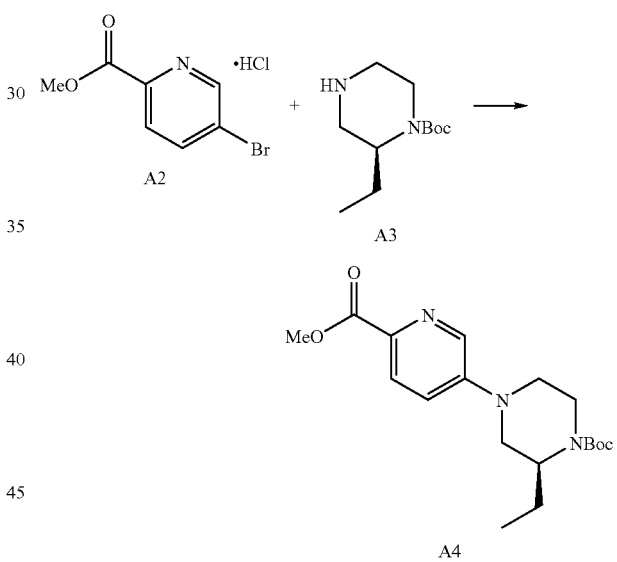

A 250 ml round bottom flask was charged with A2 (4 g, 15.9 mmol), 1-Boc-2-S-ethyl piperazine A3 (prepared as per Kiley et al Org. Prep. Proc. Int. 1990, 22, 761; 4.2 g, 18.6 mmol), tris(dibenzylideneacetone)dipalladium, (340 mg, 0.37 mmol), racemic-2,2'-bis(diphenylphosphino)-1,1'-binaphthyl (BINAP) (495 mg, 0.74 mmol), cesium carbonate (12g, 37.2 mmol) and toluene (80 ml). After the mixture was heated at 100° C. for 16 h, fresh tris(dibenzylidene-acetone) dipalladium (340 mg, 0.37 mmol) and BINAP (495 mg, 0.74 mmol) were added and the heating was continued for 3 days. The solvent was removed in vacuo, and the residue was suspended in a 100 ml portion of ethyl acetate. This mixture was extracted with water and brine, dried over sodium sulfate, and concentrated in vacuo. Purification of the residue via silica gel flash chromatography (5% methanol/95% DCM) yielded 5.3 g of a partially purified material which was used directly in the next step. M+H=350

EXAMPLE 3

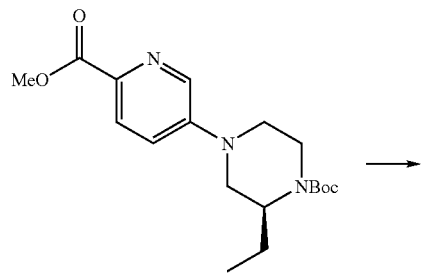

A4

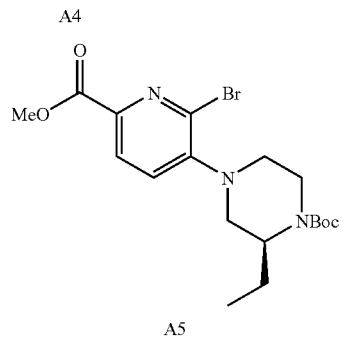

A5

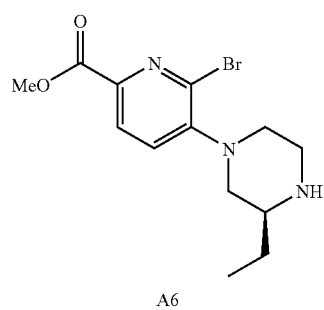

A6

Intermediate A4 (5.28 g, 15.1 mmol) was stirred with N-bromo-succinimide (5.4 g, 30.2 mmol) in 30 ml DMF for 24 h at rt. The solvent was removed in vacuo and the residue was directly purified via flash silica gel chromatography eluted with 50% ethyl acetate/50% hexanes to yield A5 (1.22 g, 19% yield, M+H=428) Further elution of the column with 10% 7N ammonia in methanol/90% DCM yielded A6 (1 28 g, 25%, M+H=328).

EXAMPLE 4

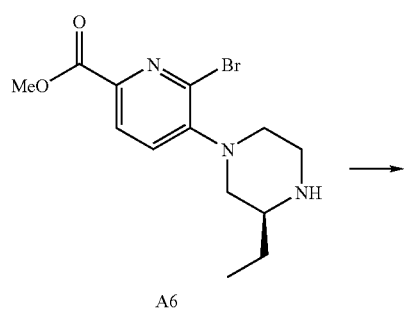

A6

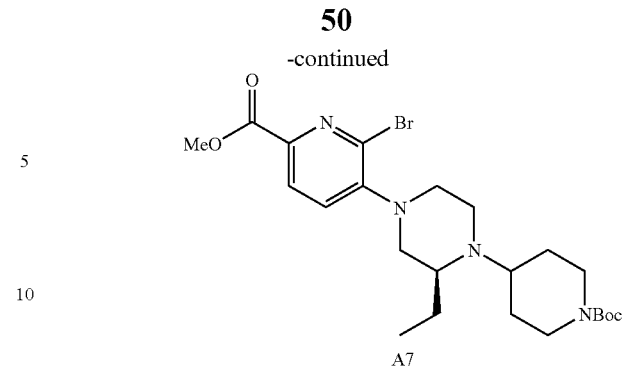

A7

Intermediate A5 (1.22 g 2.8 mmol), was deprotected by stirring in a mixture of TFA (25 ml) and DCM (75 ml) for 30 min followed by removal of the TFA and DCM in vacuo. The resultant residue was combined with previously purified A6 (see above, 1.28 g, 3.9 mmol) in dichloroethane (20 ml) and triethylamine (0.42 ml, 3 mmol) was added. To this solution of A6 (6.75 mmol total) was added sodium triacetoxyborohydride (2.85 g, 13.5 mmol) and 1-Boc-4-piperidone (2.67 g, 13.5 mmol). After stirring at rt for 16 h, OCM (50 ml) was added and the mixture was extracted with saturated sodium bicarbonate and brine, dried over sodium sulfate, and the solvent was removed in vacuo. The resultant residue was purified by flash silica gel chromatography to yield A7 (1.89 g, M+H=512). Although contaminated with Boc-piperinol, this material was used directly in the subsequent step.

EXAMPLE 5

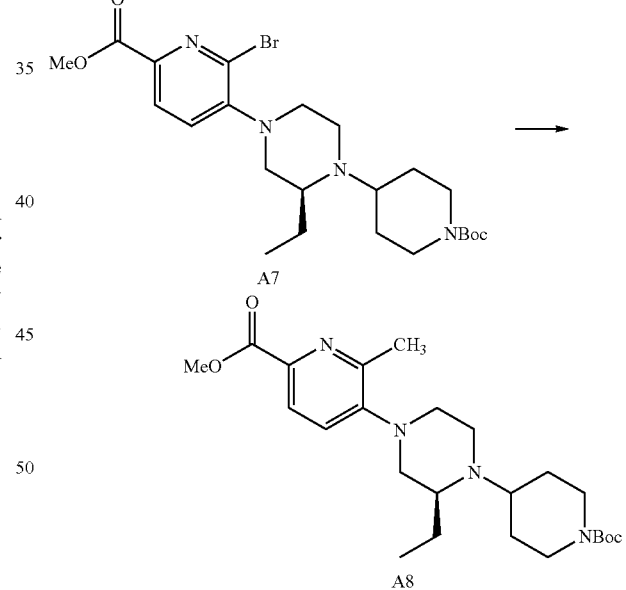

Intermediate A7 (1.89 g, 3.7 mmol) was combined with methylboronic acid (666 mg, 11.1 mmol), potassium carbonate (2.4g, 17.6 mmol), and trans-dichiorobis(triphenylphosphine)palladium (II) (260 mg, 0.37 mmol) in anhydrous DMF (10ml) and heated to 90° C. for 16 h. The solvent was removed in vacuo and the resultant residue was taken up in ethyl acetate (50 ml) and extracted with saturated sodium bicarbonate and brine. The organic layer was dried over sodium sulfate, concentrated in vacuo, and purified by silica gel flash chromatography eluted with 5% methanol/95% DCM to yield intermediate A8 (960 mg, 20% yield). M+H=447

EXAMPLE 6

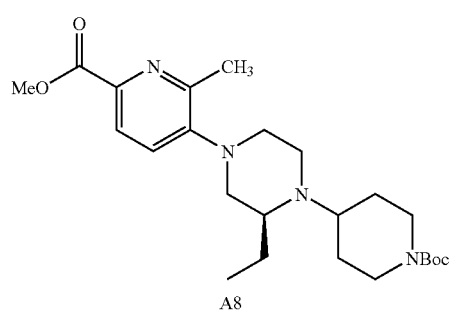
A8

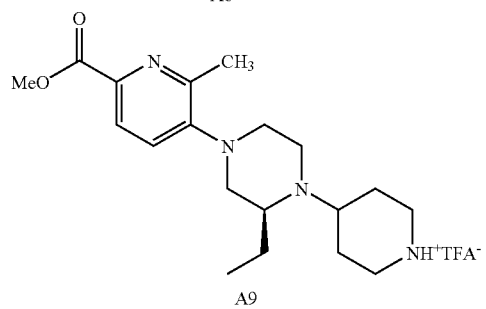
A9

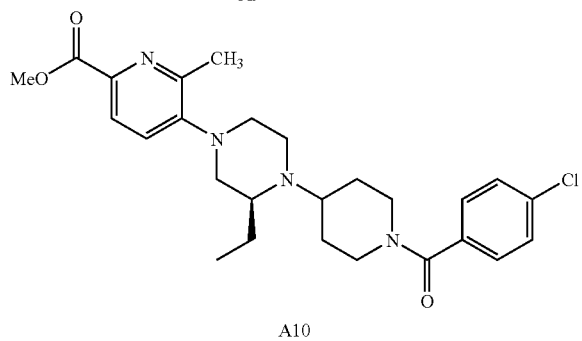
A10

The Boc protecting group of intermediate A8 (960 mg, 2.16 mmol) was removed by stirring with 10 ml TFA in 20 ml DCM for 45 min. Removal of the solvent yielded the deprotected TFA salt A9. An aliquot of A9 (0.86 mmol) was stirred with 4-chlorobenzoyl chloride (0.17 ml, 1.29 mmol) and triethylamine (0.36 ml, 2.58 mmol) in 5 ml DCM for 16 hr. This mixture was washed with saturated sodium bicarbonate and brine, dried over sodium sulfate, concentrated in vacuo, and purified by silica gel flash chromatography to yield A10 (85 mg, 0.18 mmol, 20%). M+H=485

Alternate Route to Intermediate 10

EXAMPLE 7

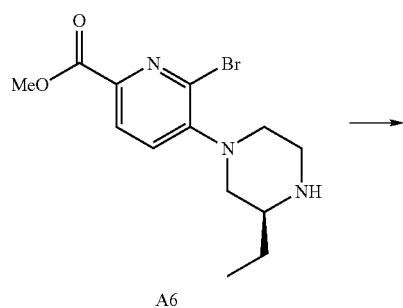
A6

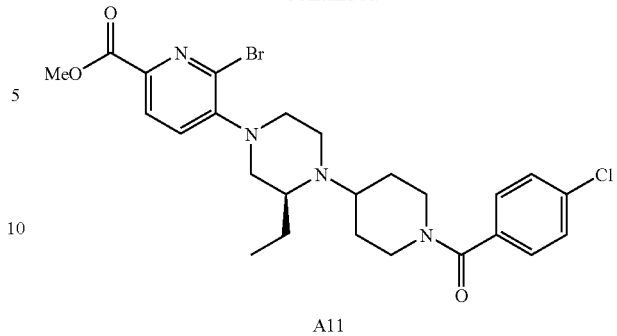
A11

To a solution of A6 (8.4 mmol) in 20 ml dichloroethane was added sodium triacetoxyborohydride (3.5 g, 16.8 mmol), 1-(4-chlorobenzoyl)-piperidin-4-one (3.28 g, 13.8 mmol), and trethylamine (2.3 ml, 16.8 mmol). After stirring at rt for 16 h, DCM (50 ml) was added and the mixture was extracted with saturated sodium bicarbonate and brine, dried over sodium sulfate, and the solvent was removed in vacuo. The resultant residue was purified by flash silica gel chromatography to yield A11 (3.2 g, M+H=549). Although contaminated with Boc-piperinol, this material was used directly in subsequent step.

EXAMPLE 8

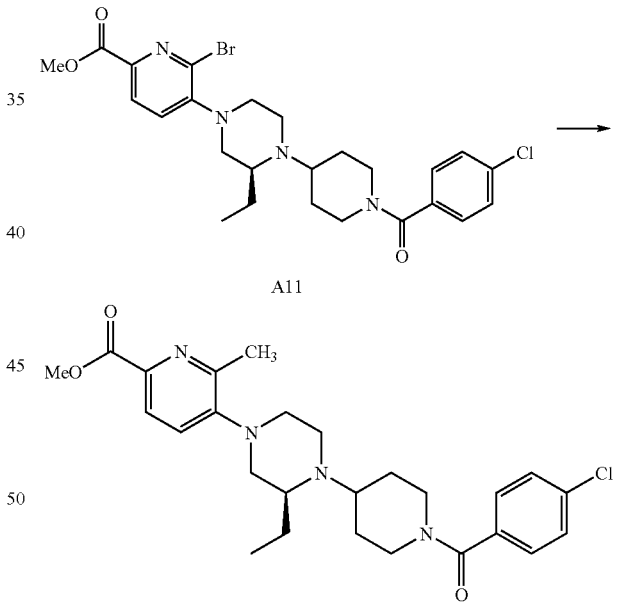

Intermediate A11 (3.2 g, 5.8 mmol) was combined with methylboronic acid (1.0 g, 17.4 mmol), potassium carbonate (3.8 g, 4.75 mmol), and trans-dichlorobis(triphenylphosphine)palladium (II) (405 mg, 0.58 mmol) in anhydrous DMF (25 ml) and heated to 90° C. for 16 h. DMF was removed in vacuo and the residue was extracted between ethyl acetate and saturated sodium bicarbonate. The organic layer was washed with brine, dried over sodium sulfate, concentrated in vacuo, and purified by silica gel flash chromatography to yield compound A10 (1.1 g, 39%).

EXAMPLE 9

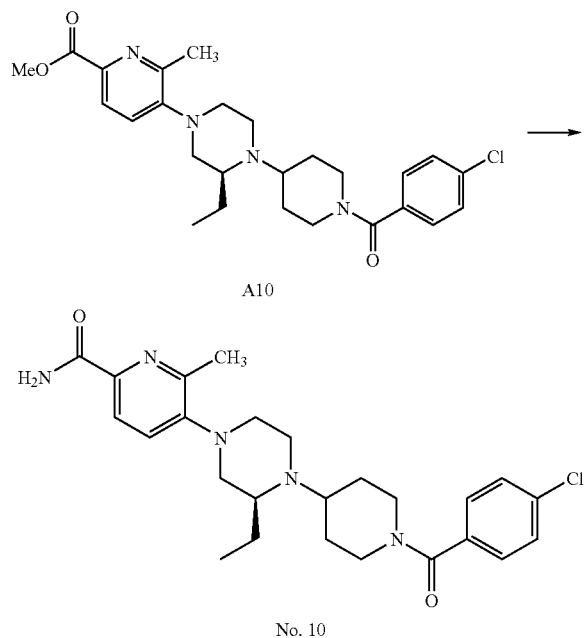

A screw top 50 ml vessel was charged with A10 (0.075 g, 0.15 mmole), 10 ml dioxane, and ammonia (10 ml, 0.5 N in dioxane). The solution was heated to 80° C. overnight in a sealed vessel. The reaction was cooled and concentrated to a clear oil. Purification on silica get afforded compound No. 10 in 70% yield as a semi-solid. M+H=471

EXAMPLE 10

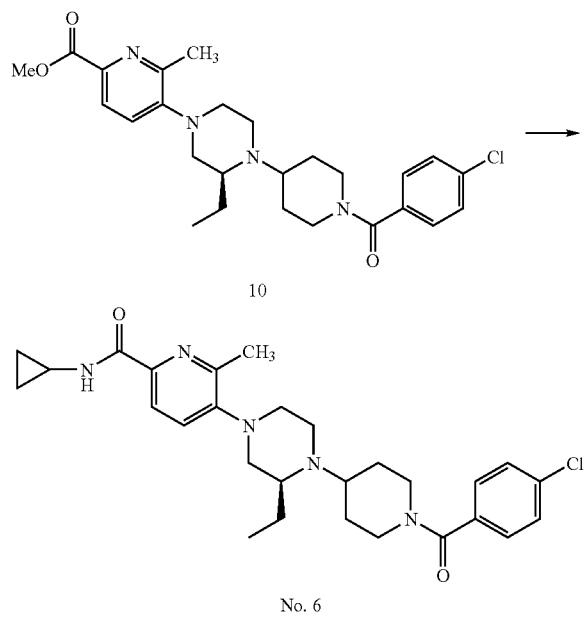

A screw top 50 ml vessel was charged with A10 (0.075 g, 0.15 mmole), 10 ml dioxane, and Cyclopropylamine (0.1 g, 1.75 mmol). The solution was heated to 80° C. overnight in a sealed vessel. The reaction was cooled and concentrated to a clear oil. Purification on silica gel afforded compound No. 6 in 70% yield as a semi-solid. M+H=511

EXAMPLE 11

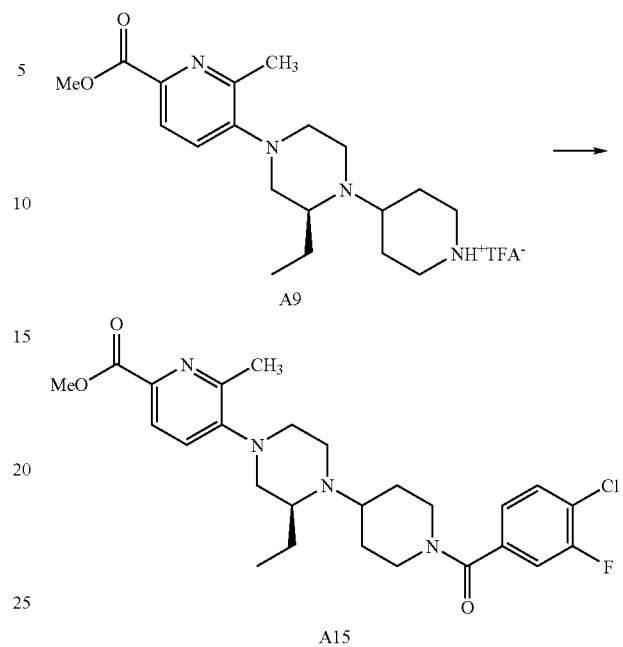

An aliquot of A9 (0.65 mmol) was stirred with 4-chloro-3-fluorobenzoic acid (170 mg, 0.98 mmol), EDCl (250 mg, 1.3 mmol), and diisopropyl-ethylamine (0-57 ml, 3.2mmol) in 5 ml DMF for 16 hr. This mixture was diluted with ethyl acetate (50 ml), washed with water and brine, dried over sodium sulfate, concentrated in vacuo, and purified by preparative reverse phase HPLC (Sunfire™ 19×100 mm 5μ C18 columns 8 min gradient: 10%→40% acetonitile/water with 0.1% TFA) to yield A15 (140 mg, 35%). M+H=503

EXAMPLE 12

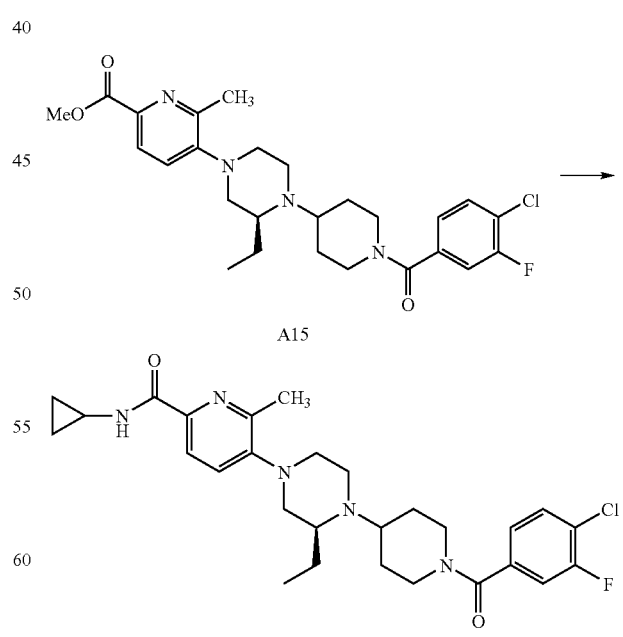

A screw top 50 ml vessel was charged with A15 (0.085 g, 0.17 mmole), 10 ml dioxane, and Cyclopropylamine (0.1 g, 1.75 mmol). The solution was heated to 80° C. overnight in a sealed vessel. The reaction was cooled and concentrated to a clear oil. Purification on silica gel afforded compound No. 5 in 84% yield as a semi-solid. M+H=529

EXAMPLE 13

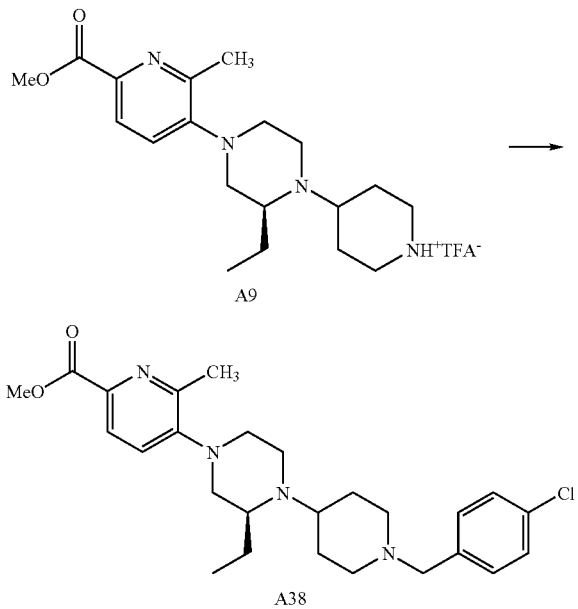

An aliquot of A9 (0.65 mmol) was stirred with 4-chlorobenzylbromide (113 mg, 0.7 mmol), EDCI (250 mg, 1.3 mmol), and diisopropyl-ethylamine (0.57 ml, 3.2 mmol) in 5 ml DMF for 16 hr. This mixture was diluted with ethyl acetate (50 ml), washed with water and brine, dried over sodium sulfate, concentrated in vacuo, and purified by on silica to afford A38 (200 mg) M+H=471

EXAMPLE 13

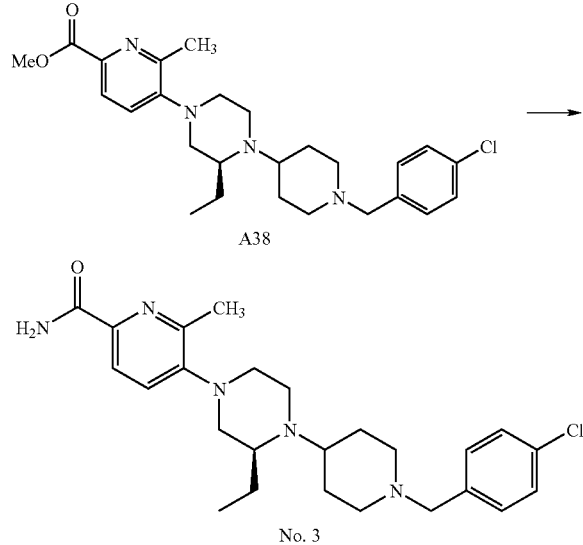

Compound No. 3 was prepared with a similar procedure to example 9 above. No. 3 M+H=457

EXAMPLE 14

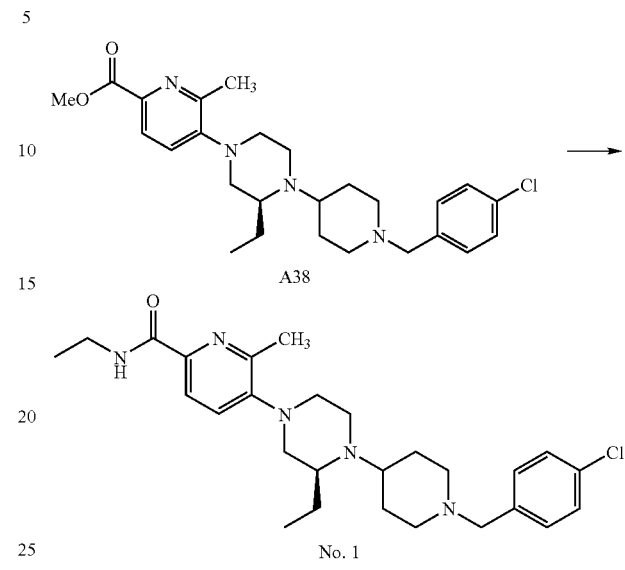

A screw top 25 ml vessel was charged with A38 (0.02 g, 0.04 mmole), and 2 N ethylamine in methanol (1 ml, 2 mmol). The solution was heated to 60° C. overnight in a sealed vessel. The reaction was cooled and concentrated to a clear oil. Purification on silica gel afforded compound No. 1 in 54% yield as a semi-solid. M+H=485

EXAMPLE 15

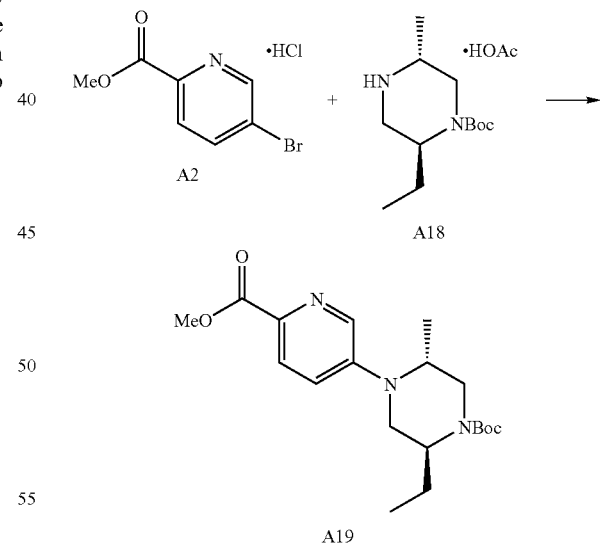

A 250 ml round bottom flask was charged with A2 (2 g, 9.4 mmol), 1-Boc-2(S)-ethyl-5(R)-methylpiperazine acetic acid salt A18 (2,2 g, 9.4 mmol) tris(dibenzylideneacetone)dipalladium ((172 mg, 0.19 mmol), racemic-2,2'-bis(diphenylphosphino)-1,1'-binaphthyl (BINAP) (250 mg, 0.38 mmol), cesium carbonate (6.1 g, 18.8 mmol) and toluene (50 ml). After the mixture was heated at 100° C. for 16 h, fresh tris(dibenzylideneacetone)dipalladium (0), (172 mg, 0.149 mmol) and BINAP (250 mg, 0.38 mmol) were added and the heating was continued for 3 further days. The solvent was removed in vacuo, and the residue was suspended in a 100 ml portion of ethyl acetate. This mixture was extracted with water and brine, dried over sodium sulfate, and concentrated in vacuo. Purification of the residue via silica gel flash chromatography column (gradient 50% ethylacetate/50% hexanes→5% methanol/195% DCM) yielded A19 (1.7 g, 50%). M+H=364

EXAMPLE 16

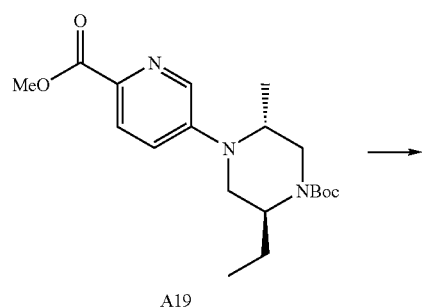

A19

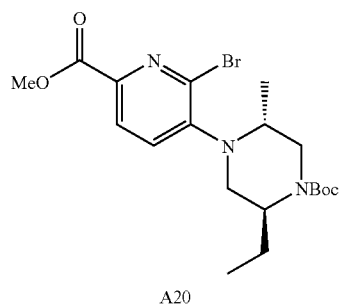

A20

Compound A19 (443 mg, 1.2 mmol) and N-bromosuccinimide (280 mg, 1.6 mmol) were stirred in DMF (3 ml) for 16 h at rt. DMF was removed in vacuo and the residue was extracted between ethyl acetate and saturated sodium bicarbonate. The ethyl acetate layer was washed with brine, dried over sodium sulfate, concentrated in vacuo, and purified by silica gel flash chromatography (50% ethylacetate/50% hexanes) to yield bromide A20 (194 mg, 36.1%) M+H=442

EXAMPLE 17

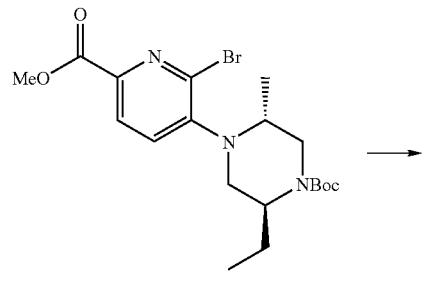

A20

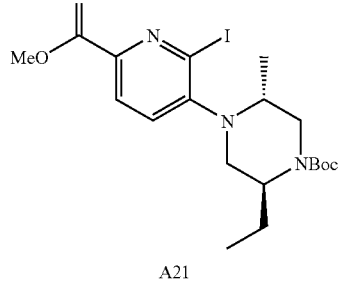

A21

Intermediate A20 (435 mg, 0.98 mmol), copper(I) iodide (10 mg, 0.049 mmol), sodium iodide (295 mg, 1.97 mmol) and N,N'-dimethylcyclohexanediamine (16 µl, 0.098 mmol) were combined in 1,4-dioxane (2 ml) and heated to 110° C. under argon for 16 h. The solution was allowed to cool to rt and 30% aqueous ammonia (5 ml) was added. The mixture was poured into water (20 ml) and extracted with DCM (3 times). The organics were dried over magnesium sulfate and concentrated in vacuo. Purification by silica gel flash chromatography (5% methanol/95% DCM) yielded iodide A21 (319 mg, 66%). M+H=490

EXAMPLE 18

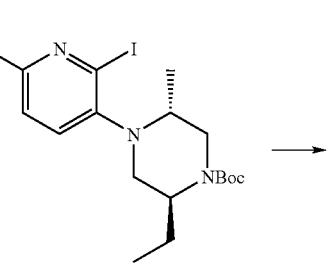

A21

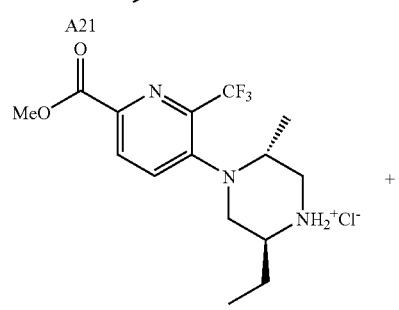

A22

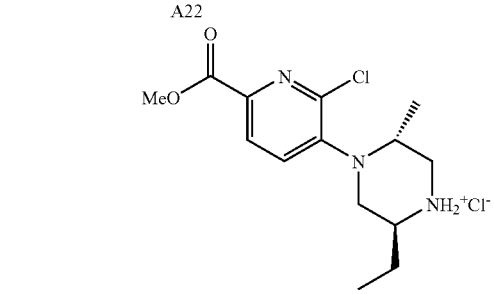

A23

Iodide A21 (221 mg, 0.45 mmol) was dissolved in DMF (2 ml) and heated to 100° C. for 16 h in the presence of Methyl chlorodifluoroacetate (96 μl, 0.9 mmol), copper(I) iodide (86 mg, 0.45 mmol), and potassium fluoride (26 mg, 0.45 mmol). After removing the DMF in vacuo, the residue was extracted between DCM (3 ml) and 10% ammonium hydroxide (3 ml). The aqueous layer was further extracted with DCM (2×3 ml) and the combined organic layers were dried over sodium sulfate, filtered, and concentrated in vacuo. Mass spectral analysis indicated a mixture of chlorinated (M+H=398) and trifluoromethylated (M+H=432) products. The crude material was treated with 4N HCl in 1,4-dioxane (5 ml) for 30 minutes and the solvent was removed in vacuo to yield a mixture of A22 and A23 which was directly carried to the next step.

EXAMPLE 19

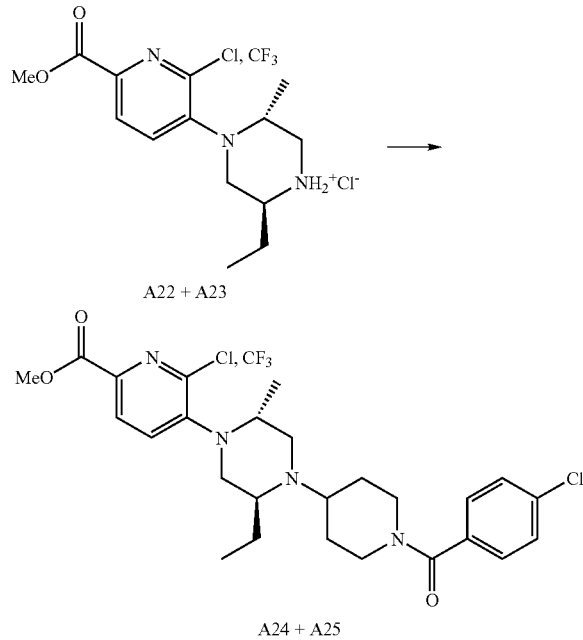

A22 + A23

A24 + A25

The mixture of A22 and A23 was stirred at rt with 1-(4-chlorobenzoyl)-piperidin-4-one (107 mg, 0.45 mmol), sodium triacetoxyborohydride (95 mg, 0.45 mmol) and triethylamine (0.2 ml, 1.35 mmol) in 1,2-dichloroethane (3 ml) for 16 h. The reaction was quenched with saturated sodium bicarbonate (2 ml), extracted with DCM (3×2 ml), dried over sodium sulfate, concentrated in vacuo and purified by silica gel flash chromatography (5% methanol/95% DCM) to give a co-eluting mixture (228 mg) of chloride A24 (M+H=519) and trifluoromethyl-substituted A25 (M+H=553).

PREPARATIVE EXAMPLE 20

Alternate Piperazine Starting Material

Step A

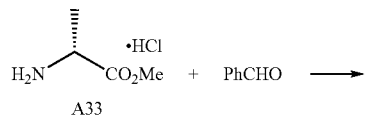

A33

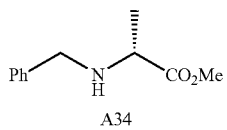

A34

Benzaldehyde (19 mL, 19 g, 0.18 mol) was added to a solution of D-alanine methyl ester hydrochloride (25 g, 0.18 mol) in dry CH$_2$Cl$_2$ (300 mL). The solution was stirred at 22° C. for 19 h. The reaction mixture was cooled with an ice-water bath and solid sodium triacetoxyborohydride (46 g, 0.22 mol) was added in portions over ~15 min. The cooling bath was removed and the milky white solution was stirred at 22° C. for 7 h. The solvent was removed by rotary evaporation under reduced pressure and the resulting slush was partitioned between EtOAc (~100 mL) and 1 N HCl (~400 mL). The aqueous layer was extracted with EtOAc (~50 mL). The aqueous layer was adjusted to pH~10 with 1 N NaOH (450 mL) and the milky aqueous layer was extracted immediately with EtOAc (3×250 mL). The combined organic layers were washed with brine (~250 mL), dried over anhydrous MgSO$_4$, filtered and concentrated under reduced pressure to afford N-benzyl-D-alanine methyl ester (28 g, 80%) as a colorless semi-solid.

Step B.

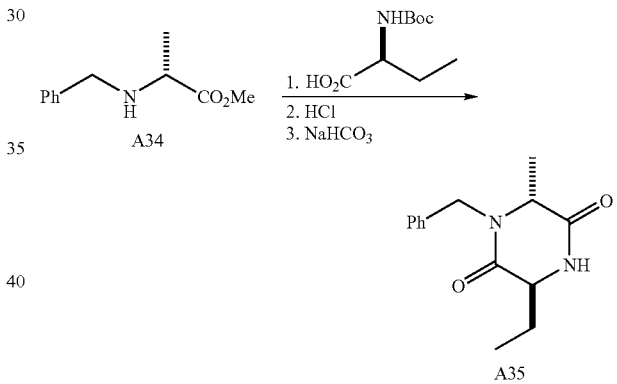

To a solution of N-benzyl-D-alanine methyl ester (28 g, 0,1 5 mol) and EDCl.HCl (30.6 g, 0.160 mmol) in CH$_2$Cl$_2$ (250 mL) was added a solution of N-Boc-2(S)-aminobutyric acid (29.5 g, 0.145 mol; Anaspec, Inc.) in CH$_2$Cl$_2$ (100 mL). The reaction mixture was stirred at 22° C. for 16 h. Additional N-Boc-2(S)-aminobutyric acid (5.9 g, 29 mmol) and EDCl.HCl (11.1 g, 58 mmol) and DMF (20 mL) were added. After 1 day, the solvents were removed under reduced pressure, and the residue was dissolved in EtOAc. The organic solution was washed with 0.5 N aqueous HCl, saturated aq. sodium carbonate, brine, and was then dried over anhydrous sodium sulfate. Subsequent filtration and concentration gave a colorless oil The oil was dissolved in CH$_2$Cl$_2$ (200 mL) and HCl gas was bubbled into the stirred solution for 1.5 h. After removal of solvent under reduced pressure, the resulting white solid was suspended in EtOAc (500 mL) and aqueous NaHCO$_3$ solution (150 mL). The mixture was stirred at rt for 18 h. The organic layer was separated, washed with brine, dried over anhydrous MgSO$_4$, filtered, and concentrated to give compound A35 (21.9 g, 61% over 2 steps).

Step C.

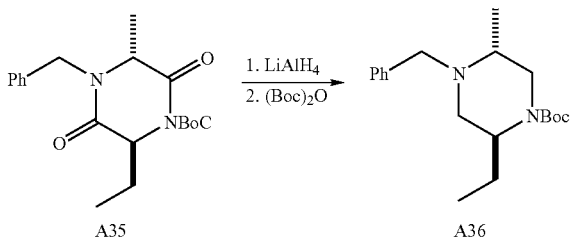

The diketopiperazine A35 (21.9 g, 89 mmol) was dissolved in dry THF (500 mL). Powdered LiAlH$_4$ (10.1 g, 267 mmol) was added cautiously and in portions over ~30 min. The reaction mixture was stirred at 22° C. for 1 h, at 65° C. for 1 d, and then at 22° C. for a further 24 h. The reaction was quenched by cautious dropwise addition of water (10 mL) over 1 h. 1 N aqueous NaOH solution (20 mL) and water (30 mL) were added sequentially and the milky white reaction mixture was stirred at rt for 1 h. The white gelatinous precipitate that formed was removed by filtration through Celite®. The filter cake was washed copiously with EtOAc (~500 mL). The combined filtrates were evaporated. The residue was dissolved in Et$_2$O (~500 mL) and then taken to dryness to afford 2(S)-ethyl-4-benzyl-5(R)-methylpiperazine (18.4 g, 93%) as a pale golden yellow oil.

The piperazine above (18.3 g, 84 mmol) was dissolved in CH$_2$Cl$_2$ (40 mL) and solid di-t-butyl dicarbonate (18.3 g, 84 mmol) was added. After stirring for 30 min at rt, the solvent was removed and the resulting yellow liquid was purified by flash column chromatography, eluting with 3:1 hexanes-Et$_2$O, to afford 1-Boc-2(S)-ethyl-4-benzyl-5(R)-methylpiperazine (A36) as a clear, colorless liquid (24.9 g, 93%).

Step D,

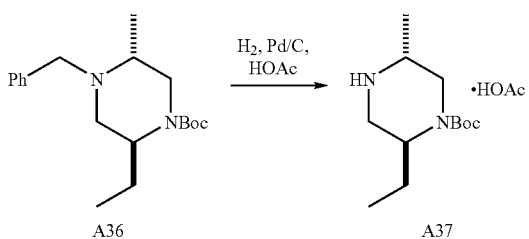

A mixture of 1-Boc-2(S)-ethyl-4-benzyl-5(R)-methylpiperazine (A36; 13.6 g, 43 mmol), glacial acetic acid (2.5 mL) and 10% Pd/C (4.5 g) in methanol (150 mL) was shaken under H$_2$ atmosphere (50 psi) for 24 h. The mixture was filtered through Celite® and the filter cake was washed copiously with EtOAc (~500 mL). The combined filtrates were dried over anhydrous MgSO$_4$, filtered, and concentrated under reduced pressure to afford a clear colorless oil. Further co-evaporation with CH$_2$Cl$_2$ (200 mL) and Et$_2$O (2×200 mL) gave the desired 1-Boc-2(S)-ethyl-5(R)-methylpiperazine acetic acid salt (A37, 9.7 g) as a viscous oil.

Piperazine A37 may be used in place of piperazine or a substituted piperazine in the above examples.

Following Analogous Procedure for the Preparation of Compounds no. 1, 3, 5, 6 and 10 above the following compounds were prepared.

| NO. from table 1 | MW |
|---|---|
| 2 | 545.65 |
| 4 | 505.59 |
| 7 | 544.53 |
| 8 | 511.62 |
| 9 | 542.10 |
| 11 | 578.08 |
| 12 | 452.00 |
| 13 | 457.02 |
| 14 | 470.02 |

BIOLOGICAL EXAMPLES

The inventive compounds can readily be evaluated to determine activity at The CXCR3 receptors by known methods, such as, for example, Development of Human CXCR3 (N-delta 4) Binding Assay.

Cloning and Expression of Human CXCR3 (N-delta 4):

The DNA encoding human CXCR3 was cloned by PCR using human genomic DNA (Promega, Madison, Wis.) as a template. The PCR primers were designed based on the published sequence of human orphan receptor GPR9 (1) with incorporated restriction sites, a Kozak consensus sequence, CD8 leader and Flag tag. The PCR product was subcloned into the mammalian expression vector pME18neo, a derivative of the SR-alpha expression vector (designated as pME18Sneo-hCXCR3 (N-delta 4).

IL-3-dependent mouse pro-B cells Ba/F3 were transfected by electroporation in 0.4 ml Dulbecco's PBS containing 4×10$^6$ cells with 20 μg of pME18Sneo-hCXCR3 (N-delta 4) plasmid DNA. Cells were pulsed at 400 Volts, 100 OHMs, 960 μFd. The transfected cells were under selection with 1 mg/ml G418 (Life Technologies, Gaithersburg, Md.). G418-resistant Ba/F3 clones were screened for CXCR3 expression by specific binding of [$^{125}$I] IP-10 (NEN Life Science Products, Boston, Mass.).

Preparation of Ba/F3-hCXCR3 (N-delta 4) Membranes

Ba/F3 cells expressing human CXCR3 (N-delta 4) were pelleted and resuspended in the lysis buffer containing 10 mM HEPES, pH 7.5 and Complete® protease inhibitors (1 tablet per 100 ml) (Boehringer Mannheim, Indianapolis, Ind.) at a cell density of 20×10$^6$ cells per ml. After 5 minutes incubation on ice, cells were transferred to 4639 cell disruption bomb (Parr Instrument, Moline, Ill.) and applied with 1,500 psi of nitrogen for 30 minutes on ice. Large cellular debris was removed by centrifugation at 1,000×g. Cell membrane in the supernatant was sedimented at 100,000×g. The membrane was resuspended in the lysis buffer supplemented with 10% sucrose and stored at −80° C. Total protein concentration of the membrane was determined by BCA method from Pierce (Rockford, Ill.).

Human CXCR3 (N-delta 4) Scintillation Proximity Assay (SPA)

For each assay point, 2 μg of membrane was preincubated for 1 hr with 300 μg wheat germ agglutinin (WGA) coated SPA beads (Amersham, Arlington Heights, Ill.) in the binding buffer (50 mM HEPES, 1 mM CaCl$_2$, 5 mM MgCl$_2$, 125 mM NaCl, 0.002% NaN$_3$, 1.0% BSA) at room temperature. The beads were spun down, washed once, resuspended in the binding buffer and transferred to a 96-well Isoplate (Wallac, Gaithersburg, Md.). 25 pM of [$^{125}$I] IP-10 with tested compounds in a series of titration were added to start the reaction. After 3 hr reaction at room temperature, the amount of [$^{125}$I] IP-10 bound to the SPA beads was determined with a Wallac 1450 Microbeta counter.

The Ki values for the various example compounds of the present invention are given in the afore-mentioned Table 1. From these values, it would be apparent to the skilled artisan that the compounds of the invention have excellent utility CXCR3 antagonists.

While the present invention has been describe in conjunction with the specific embodiments set forth above, many alternatives, modifications and variations thereof will be apparent to those of ordinary skill in the art. All such alternatives, medications and variations are intended to fall within the spirit and scope of the present invention.

Each and every reference referred to in this Application is incorporated herein by reference in its entirety for all purposes.

What is claimed is:

1. A compound having the general structure shown in Formula 1:

Formula 1 or a pharmaceutically acceptable salt thereof wherein:
G is —C≡N or

X is N;
Z is N, or NO;
$R^1$ and $R^2$ are independently selected from the group consisting of H, alkyl, cycloalkyl, aryl, and hydroxyalkyl; or alternatively, the N taken together with the $R^1$ and $R^2$ forms —N=C(NH$_2$)$_2$,
$R^3$, $R^5$ and $R^6$ moieties can be the same or different, each being independently selected from the group consisting of H, alkyl, CF$_3$, OCF$_3$, haloalkyl, halogen, —N(R$^{30}$)$_2$ and —OR$^{30}$;
$R^7$ and $R^8$ are the same or different, each being independently selected from the group consisting of H, and alkyl; or alternatively $R^7$ and $R^8$ taken together with the carbon atom to which they are shown attached is —C=O;
the $R^{10}$ moieties can be the same or different, each being independently selected from the group consisting of H, alkyl, hydroxyl, —N(R$^{30}$)$_2$, —OR$^{30}$, and halogen; or wherein two $R^{10}$ moieties together on the same carbon atom form —C=O;
the $R^{11}$ moieties can be the same or different, each being independently selected from the group consisting of H, alkyl, hydroxyl, —N(R$^{30}$)$_2$, —OR$^{30}$, and halogen; or wherein two $R^{11}$ moieties together on the same carbon atom form —C=O;
$R^{12}$ is selected from the group consisting of H, alkyl, haloalkyl and CF$_3$;
D is a phenyl, which is unsubstituted or substituted with 1-5 independently selected $R^{20}$ moieties;
the $R^{20}$ moieties can be the same or different, each being independently selected from the group consisting of alkyl, cyano, halogen, haloalkyl, haloalkoxy, —(CH$_2$)$_q$NH$_2$, —(CH$_2$)$_q$NHR$^{31}$, —(CH$_2$)$_q$N(R$^{31}$)$_2$, —N(R$^{30}$)$_2$, OR$^{30}$, —SO$_2$N(R$^{30}$)$_2$, and —SO$_2$(R$^{31}$);
Y is selected from the group consisting of —(CR$^{13}$R$^{13}$)$_r$—, —CHR$^{13}$C(=O)—, and —C(=O)—;
the $R^{13}$ moieties can be the same or different, each being independently selected from the group consisting of H, alkyl, cycloalkyl, and alkoxy;
the $R^{30}$ moieties can be the same or different, each being independently selected from the group consisting of H and alkyl;
the $R^{31}$ moieties are independently alkyl;
m is 0 to 4;
n is 0 to 4;
each q can be the same or different, each being independently selected from 1 to 5; and
r is 1 to 4;
wherein:
"alkyl" refers to C$_1$-C$_6$ alkyl;
"cycloalkyl" refers to C$_3$-C$_{10}$ cycloalkyl; and
"aryl" refers to C$_6$-C$_{10}$ aryl.

2. The compound according to claim 1, wherein G is —C≡N.

3. The compound according to claim 1, wherein G is

4. The compound according to claim 3, wherein $R^1$ and $R^2$ are independently selected from the group consisting of H, alkyl, hydroxyalkyl, and cycloalkyl.

5. The compound according to claim 3, wherein $R^1$ and $R^2$ are independently selected from the group consisting of H, —CH$_3$, —CH$_2$CH$_3$, —CH$_2$CH$_2$OH, and cyclopropyl.

6. The compound according to claim 1, wherein $R^3$ is selected from the group consisting of H, alkyl, alkoxy, halogen, and haloalkyl.

7. The compound according to claim 1, wherein $R^3$ is selected from the group consisting of —H, —CH$_3$, OCH$_3$, —Cl and —CF$_3$.

8. The compound according to claim 1, wherein $R^5$ is selected from the group consisting of H, alkyl, —OR$^{30}$, —N(R$^{30}$)$_2$, and halogen.

9. The compound according to claim 1, wherein $R^5$ is selected from the group consisting of H, CH$_3$, OH, NH$_2$, and F.

10. The compound according to claim 8, wherein $R^5$ is H.

11. The compound according to claim 1, wherein $R^6$ is selected from the group consisting of H, alkyl, —OR$^{30}$, —N(R$^{30}$)$_2$, and halogen.

12. The compound according to claim 1, wherein $R^6$ is selected from the group consisting of H and alkyl.

13. The compound according to claim 1, wherein $R^6$ is selected from the group consisting of H, CH$_3$, OH, NH$_2$, and F.

14. The compound according to claim 1, wherein $R^6$ is selected from the group consisting of —H and —CH$_3$.

15. The compound according to claim 3, wherein $R^7$ and $R^8$ are both H, or $R^7$ and $R^8$ taken together with the carbon atom to which they are shown attached is —C=O.

16. The compound according to claim 1, wherein $R^{10}$ is independently selected from the group consisting of alkyl, hydroxyl, and alkoxy, or wherein two $R^{10}$ moieties together on the same carbon atom form —C=O, and m is 1-2.

17. The compound according to claim 16, wherein $R^{10}$ is alkyl, and m is 1-2.

18. The compound according to claim 17, wherein $R^{10}$ is selected from the group consisting of —CH$_3$ and —CH$_2$CH$_3$.

19. The compound according to claim 1, wherein $R^{11}$ is selected from the group consisting of H, alkyl, alkoxy, and hydroxyl, or wherein two $R^{11}$ moieties together on the same carbon atom form —C=O; and n is 1-2.

20. The compound according to claim 19, wherein $R^{11}$ is H, and n is 1.

21. The compound according to claim 1, wherein $R^{12}$ is selected from the group consisting of H, alkyl, and haloalkyl.

22. The compound according to claim 1, wherein $R^{12}$ is selected from the group consisting of H, CH$_3$, and CF$_3$.

23. The compound according to claim 22, wherein $R^{12}$ is H.

24. The compound according to claim 1, wherein Y is selected from the group consisting of: —(CHR$^{13}$)$_r$— and —C(=O)—.

25. The compound according to claim 1, wherein Y is selected from the group consisting of: —CH$_2$— and —C(=O)—.

26. The compound according to claim 1, wherein D is a phenyl optionally substituted with 1-2 $R^{20}$ moieties selected independently from the group consisting of halogen, —OR$^{30}$, alkyl, —N(R$^{30}$)$_2$, haloalkyl, cyano, —SO$_2$(R$^{31}$), —SO$_2$N(R$^{30}$)$_2$, and haloalkoxy.

27. The compound according to claim 1, wherein D is a phenyl optionally substituted with 1-2 $R^{20}$ moieties selected independently from the group consisting of halogen, hydroxyl, alkyl, alkoxy, aminoalkyl, haloalkyl, cyano, sulfonylalkyl, sulfonylamino and haloalkoxy.

28. The compound according to claim 27, wherein D is a phenyl optionally substituted with 1-2 $R^{20}$ moieties selected independently from the group consisting of halogen, alkyl, alkoxy, haloalkyl, and haloalkoxy.

29. The compound according to claim 1, wherein D is phenyl, substituted with 1-2 moieties selected independently from the group consisting of alkyl, alkoxy, —Cl, —F, and trifluoromethoxy.

30. The compound according to claim 1, wherein:
G is

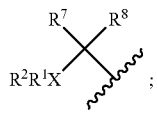;

$R^1$ and $R^2$ are independently selected from the group consisting of H, alkyl, aryl and cycloalkyl;
$R^3$, $R^5$, and $R^6$ are independently selected from the group consisting of —H, alkyl, haloalkyl, amino, aminoalkyl, alkoxy, CF$_3$, halogen, or hydroxyl;
$R^{10}$ and $R^{11}$ are independently selected from the group consisting of H, alkyl, —N(R$^{30}$)$_2$, halogen, or hydroxyl or wherein two $R^{10}$ or $R^{11}$ moieties together on the same carbon atom form —C=O; and
m and n are independently an integer from 1 to 4.

31. The compound according to claim 1, wherein:
Z is N;
G is

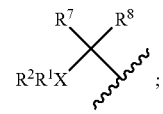;

X is N;
$R^1$ and $R^2$ are independently selected from the group consisting of H, alkyl, and cycloalkyl;
$R^3$, $R^5$, and $R^6$ are independently selected from the group consisting of —H, alkyl, haloalkyl, amino, aminoalkyl, alkoxy, CF$_3$, halogen, and hydroxyl;
$R^7$ and $R^8$ taken together with the carbon atom to which they are shown attached is —C=O; and
m and n are independently an integer from 1 to 4.

32. The compound according to claim 1, wherein:
Z is N;
G is

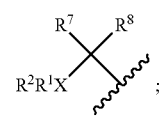;

X is N;
$R^1$ and $R^2$ are independently selected from the group consisting of H, alkyl, and cycloalkyl;
$R^3$, $R^5$, and $R^6$ are independently selected from the group consisting of —H, alkyl, haloalkyl, amino, aminoalkyl, alkoxy, CF$_3$, halogen, and hydroxyl;
$R^7$ and $R^8$ taken together with the carbon atom to which they are shown attached is —C=O;
$R^{10}$, $R^{11}$ are independently selected from the group consisting of H, alkyl, amino, aminoalkyl, halogen, or hydroxyl or wherein two $R^{10}$ or $R^{11}$ moieties together on the same carbon atom form —C=O; and
m and n are independently an integer from 1 to 4.

33. The compound according to claim 1, wherein:
Z is N;
G is

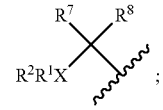;

X is N;
$R^1$ and $R^2$ are independently selected from the group consisting of H, —CH$_3$, —CH$_2$CH$_3$, cyclopropyl and alkyl;
$R^3$, $R^5$, $R^6$ is independently selected from the group consisting of H, —CH$_3$, —F, —Cl, —OH, —OCH$_3$, —OCF$_3$, NH$_2$, SO$_2$CH$_3$, and —CF$_3$;
$R^7$ and $R^8$ are both H, or $R^7$ and $R^8$ taken together with the carbon atom to which they are shown attached is —C=O;
$R^{10}$ is selected from the group consisting of —CH$_3$, —CH$_2$CH$_3$, and hydroxyl, or two $R^{10}$ moieties together on the same carbon atom form =O, and m is 1-2;

R[11] is selected from the group consisting of H and hydroxyl or two R[11] moieties together on the same carbon atom form —C=O, and n is 1;

R[12] is selected from the group consisting of H and CF$_3$;

Y is selected from the group consisting of —CH$_2$— and —C(=O)—; and

D is a phenyl, wherein ring D is substituted with 1-2 moieties selected independently from the group consisting of —Cl, —CH$_3$, —F, —OH, OCH$_3$, OCF$_3$, NH$_2$, NH(CH$_3$)$_2$, SO$_2$CH$_3$, SO$_2$NH$_2$, and trifluoromethyl.

34. The compound according to claim 33, wherein:

Z is N;

G is

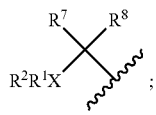

X is N;

R[1] and R[2] are independently selected from the group consisting of H, —CH$_3$, —CH$_2$CH$_3$, cyclopropyl and alkyl;

R[3], R[5], R[6] is independently selected from the group consisting of H, —CH$_3$, —F, —Cl, —OH, —OCH$_3$, —OCF$_3$, SO$_2$CH$_3$, and —CF$_3$;

R[7] and R[8] are both H, or R[7] and R[8] taken together with the carbon atom to which they are shown attached is —C=O;

R[10] is selected from the group consisting of —CH$_3$, —CH$_2$CH$_3$, and hydroxyl, or two R[10] moieties together on the same carbon atom form —C=O, and m is 1-2;

R[11] is selected from the group consisting of H and hydroxyl or two R[11] moieties together on the same carbon atom form —C=O, and n is 1;

R[12] is selected from the group consisting of H and CF$_3$;

Y is selected from the group consisting of —CH$_2$— and —C(=O)—; and

D is a phenyl, wherein ring D is substituted with 1-2 moieties selected independently from the group consisting of —Cl, —CH$_3$, —F, —OH, NH$_2$, SO$_2$CH$_3$, and trifluoromethoxy.

35. A compound selected from the group consisting of:

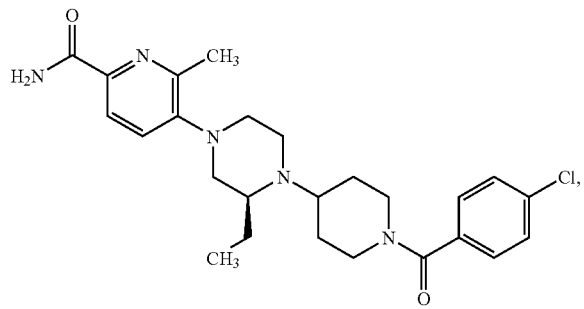

-continued

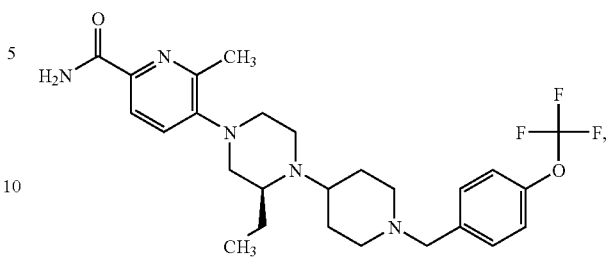

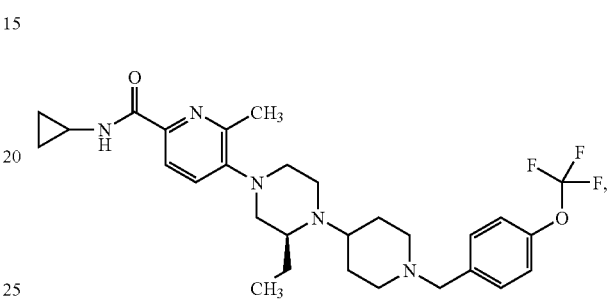

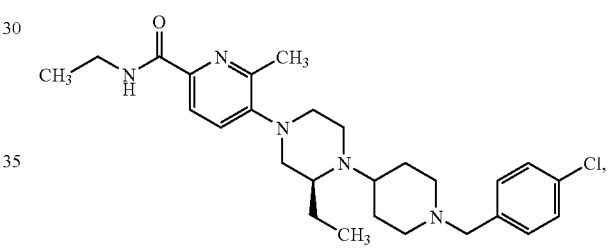

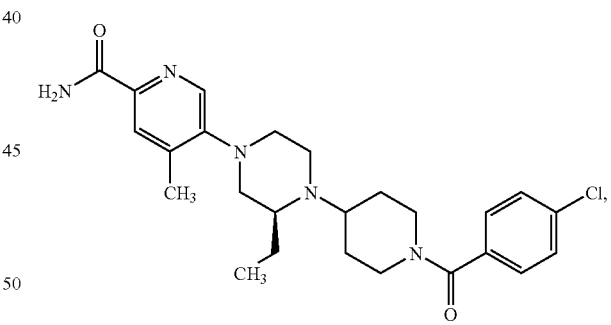

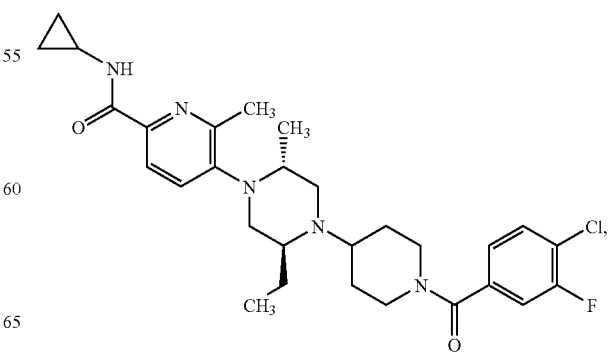

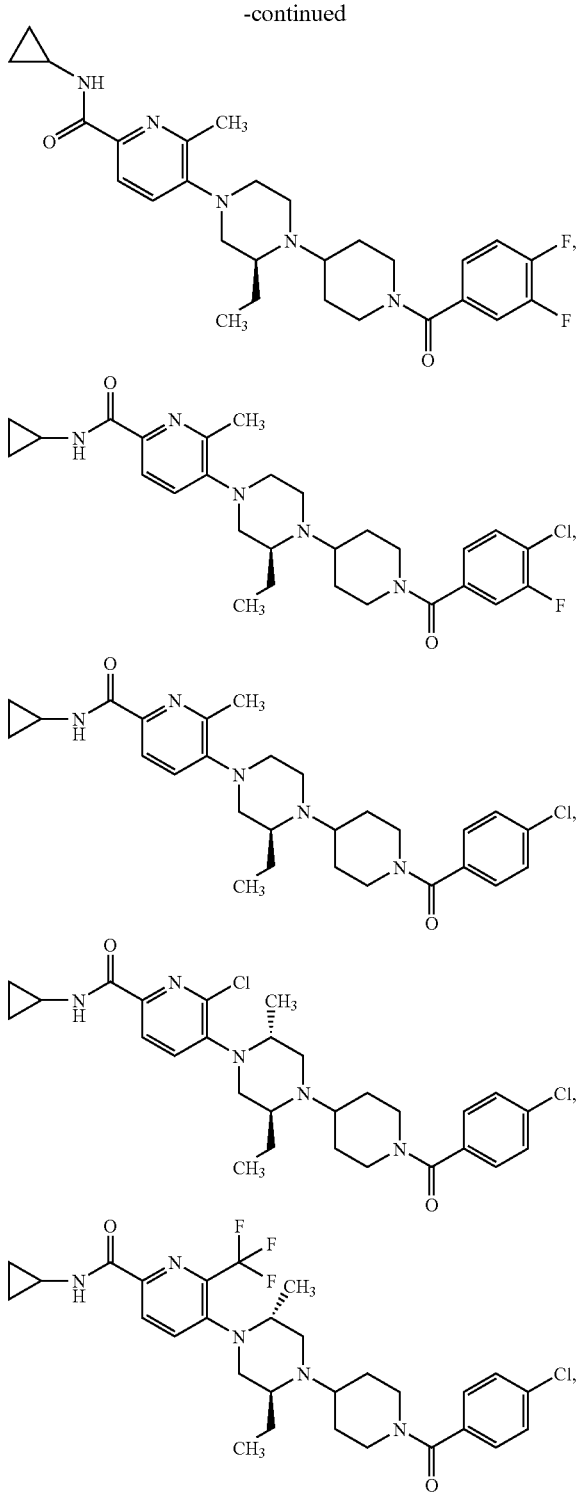

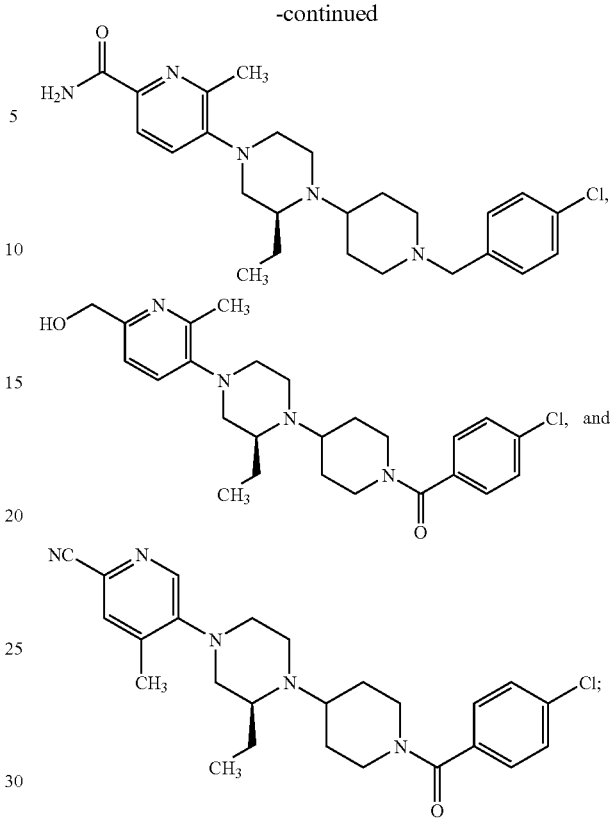

or a pharmaceutically acceptable salt thereof.

36. A compound according to claim 1, in optically pure form.

37. A pharmaceutical composition comprising at least one compound of claim 1, or a pharmaceutically acceptable salt thereof, in combination with at least one pharmaceutically acceptable carrier.

38. The pharmaceutical composition of claim 37, further comprising at least one additional agent, drug, medicament, antibody and/or inhibitor for treating a CXCR3 chemokine receptor mediated disease.

39. A pharmaceutical composition comprising at least one compound of claim 35, or a pharmaceutically acceptable salt, in combination with at least one pharmaceutically acceptable carrier.

40. The pharmaceutical composition of claim 39, further comprising at least one additional agent, drug, medicament, antibody and/or inhibitor for treating a CXCR3 chemokine receptor mediated disease.

* * * * *